(12) United States Patent
Splett et al.

(10) Patent No.: US 10,532,212 B2
(45) Date of Patent: * Jan. 14, 2020

(54) ATRIAL TRACKING IN AN INTRACARDIAC VENTRICULAR PACEMAKER

(71) Applicant: Medtronic, Inc., Minneapolis, MN (US)

(72) Inventors: Vincent E Splett, Apple Valley, MN (US); Todd J Sheldon, North Oaks, MN (US); Yong K Cho, Excelsior, MN (US); Wade M Demmer, Coon Rapids, MN (US); Mark K Erickson, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/280,538

(22) Filed: Sep. 29, 2016

(65) Prior Publication Data

US 2018/0085589 A1   Mar. 29, 2018

(51) Int. Cl.
*A61N 1/36* (2006.01)
*A61N 1/365* (2006.01)
*A61N 1/368* (2006.01)
*A61N 1/375* (2006.01)

(52) U.S. Cl.
CPC ....... *A61N 1/36578* (2013.01); *A61N 1/3682* (2013.01); *A61N 1/3684* (2013.01); *A61N 1/36585* (2013.01); *A61N 1/3756* (2013.01)

(58) Field of Classification Search
CPC .................. A61N 1/36578; A61N 1/3682
See application file for complete search history.

(56) References Cited

U.S. PATENT DOCUMENTS

| 4,485,813 | A |   | 12/1984 | Anderson et al. |
|---|---|---|---|---|
| 5,052,388 | A |   | 10/1991 | Sivula et al. |
| 5,085,215 | A | * | 2/1992 | Nappholz .......... A61N 1/36514 607/17 |
| 5,480,412 | A |   | 1/1996 | Mouchawar et al. |
| 5,496,361 | A |   | 3/1996 | Moberg et al. |

(Continued)

FOREIGN PATENT DOCUMENTS

WO         9527531 A1     10/1995

OTHER PUBLICATIONS (PCT/US2017/054412) PCT Notification of Transmittal of the International Search Report and the Written Opinion of the International Searching Authority, dated Jan. 22, 2018, 11 pages.

(Continued)

*Primary Examiner* — Eric D. Bertram

(57) ABSTRACT

An intracardiac ventricular pacemaker is configured to detect a ventricular diastolic event from a motion signal received by a pacemaker control circuit from a motion sensor. The control circuit starts an atrial refractory period having an expiration time set based on a time of the detection of the ventricular diastolic event. The control circuit detects an atrial systolic event from the motion signal after expiration of the atrial refractory period and controls a pulse generator of the pacemaker to deliver a pacing pulse to a ventricle of a patient's heart at a first atrioventricular pacing time interval after the atrial systolic event detection.

22 Claims, 9 Drawing Sheets

(56) References Cited

U.S. PATENT DOCUMENTS

| | | | |
|---|---|---|---|
| 5,507,782 A | 4/1996 | Kieval et al. | |
| 5,593,431 A | 1/1997 | Sheldon | |
| 5,683,432 A | 11/1997 | Goedeke et al. | |
| 5,836,987 A | 11/1998 | Baumann et al. | |
| 5,885,471 A | 3/1999 | Ruben et al. | |
| 5,891,176 A | 4/1999 | Bornzin | |
| 6,044,297 A | 3/2000 | Sheldon et al. | |
| 6,650,940 B1 | 11/2003 | Zhu et al. | |
| 7,127,289 B2 | 10/2006 | Yu et al. | |
| 7,130,681 B2 | 10/2006 | Gebhardt et al. | |
| 7,904,155 B2 | 3/2011 | Yu et al. | |
| 8,214,036 B2 | 7/2012 | Casset | |
| 8,233,981 B2 | 7/2012 | Casset | |
| 8,433,409 B2 | 4/2013 | Johnson et al. | |
| 8,532,785 B1 | 9/2013 | Crutchfield et al. | |
| 8,541,131 B2 | 9/2013 | Lund et al. | |
| 8,792,980 B2 | 7/2014 | Yu et al. | |
| 8,923,963 B2 | 12/2014 | Bonner et al. | |
| 8,996,109 B2 | 3/2015 | Karst et al. | |
| 9,272,146 B2 | 3/2016 | Anselmi | |
| 9,278,218 B2 | 3/2016 | Karst et al. | |
| 10,080,900 B2 | 9/2018 | Ghosh et al. | |
| 10,286,214 B2 * | 5/2019 | Demmer | A61N 1/0573 |
| 2007/0043398 A1 | 2/2007 | Ternes et al. | |
| 2012/0095521 A1 | 4/2012 | Hintz | |
| 2012/0172892 A1 | 7/2012 | Grubac et al. | |
| 2013/0325081 A1 * | 12/2013 | Karst | A61N 1/36592 607/25 |
| 2014/0121721 A1 | 5/2014 | Ghanem et al. | |
| 2015/0217119 A1 | 8/2015 | Nikolski et al. | |
| 2016/0011416 A1 | 1/2016 | Kobayashi | |
| 2016/0015287 A1 | 1/2016 | Anderson et al. | |
| 2016/0015322 A1 | 1/2016 | Anderson et al. | |
| 2016/0015984 A1 | 1/2016 | Demmer et al. | |
| 2016/0015985 A1 | 1/2016 | Cho et al. | |
| 2016/0023000 A1 | 1/2016 | Cho et al. | |
| 2016/0067486 A1 | 3/2016 | Brown et al. | |
| 2016/0067487 A1 | 3/2016 | Demmer et al. | |
| 2016/0067490 A1 | 3/2016 | Carney et al. | |
| 2016/0067500 A1 | 3/2016 | Demmer et al. | |
| 2016/0114162 A1 | 4/2016 | Sheldon et al. | |
| 2016/0114168 A1 | 4/2016 | Demmer et al. | |
| 2016/0114169 A1 | 4/2016 | Sheldon et al. | |
| 2016/0144190 A1 | 5/2016 | Cao et al. | |
| 2016/0144191 A1 | 5/2016 | Sheldon | |
| 2018/0085588 A1 | 3/2018 | Splett et al. | |

OTHER PUBLICATIONS

U.S. Appl. No. 14/964,279, filed Apr. 23, 2015.
U.S. Appl. No. 14/920,228, filed Oct. 22, 2015.
U.S. Appl. No. 14/810,559, filed Jul. 28, 2015.

* cited by examiner

US 10,532,212 B2

ATRIAL TRACKING IN AN INTRACARDIAC VENTRICULAR PACEMAKER

RELATED APPLICATION

This application is related to U.S. patent application Ser. No. 15/280,339 filed on even date herewith entitled "ATRIAL TR ACKING IN AN INTRACARDIAC VENTRICULAR PACEMAKER", herein incorporated by reference in its entirety.

TECHNICAL FIELD

The disclosure relates to an intracardiac ventricular pacemaker and associated method for detecting atrial events from a motion sensor signal and controlling atrial-synchronized ventricular pacing delivered by the pacemaker.

BACKGROUND

Implantable cardiac pacemakers are often placed in a subcutaneous pocket and coupled to one or more transvenous medical electrical leads carrying pacing and sensing electrodes positioned in the heart. A cardiac pacemaker implanted subcutaneously may be a single chamber pacemaker coupled to one transvenous medical lead for positioning electrodes in one heart chamber, atrial or ventricular, or a dual chamber pacemaker coupled to two intracardiac leads for positioning electrodes in both an atrial and a ventricular chamber. Multi-chamber pacemakers are also available that may be coupled to three leads, for example, for positioning electrodes for pacing and sensing in one atrial chamber and both the right and left ventricles.

Intracardiac pacemakers have recently been introduced that are implantable within a ventricular chamber of a patient's heart for delivering ventricular pacing pulses. Such a pacemaker may sense R-wave signals attendant to intrinsic ventricular depolarizations and deliver ventricular pacing pulses in the absence of sensed R-waves. While single chamber ventricular sensing and pacing by an intracardiac ventricular pacemaker may adequately address some patient conditions, other conditions may require atrial and ventricular (dual chamber) sensing for providing atrial-synchronized ventricular pacing in order to maintain a regular heart rhythm.

SUMMARY

In general, the disclosure is directed to a ventricular pacemaker and techniques for detecting atrial systolic events from a motion sensor signal for controlling atrial-synchronized ventricular pacing by the ventricular pacemaker. A pacemaker operating according to the techniques disclosed herein detects a ventricular diastolic event from the motion sensor signal and sets an atrial refractory period based on the timing of the ventricular diastolic event. The pacemaker detects atrial systolic events after the expiration of atrial refractory periods and sets an atrioventricular pacing interval in response to detecting atrial systolic events for providing atrial-synchronized ventricular pacing.

In one example, the disclosure provides an intracardiac ventricular pacemaker including a pulse generator configured to generate and deliver pacing pulses to a ventricle of a patient's heart via electrodes coupled to the pacemaker; a motion sensor configured to produce a motion signal including a ventricular diastolic event and an atrial systolic event; and a control circuit coupled to the motion sensor and the pulse generator. The control circuit is configured to detect the ventricular diastolic event from the motion signal; start an atrial refractory period having an expiration time set based on a time of the detection of the ventricular diastolic event; detect an atrial systolic event from the motion signal after expiration of the atrial refractory period; and control the pulse generator to deliver a pacing pulse to the ventricle at an atrioventricular pacing time interval after the atrial systolic event detection.

In another example, the disclosure provides a method performed by an intracardiac pacemaker. The method includes detecting a ventricular diastolic event from a motion signal received by the control circuit from a motion sensor; starting an atrial refractory period having an expiration time set based on a time of the detection of the ventricular diastolic event; detecting an atrial systolic event from the motion signal after expiration of the atrial refractory period; and controlling a pulse generator of the pacemaker to deliver a pacing pulse to a ventricle of a patient's heart at an atrioventricular pacing time interval after the atrial systolic event detection.

In another example, the disclosure provides a non-transitory, computer-readable storage medium storing a set of instructions which, when executed by a control circuit of an intracardiac ventricular pacemaker having a motion sensor, cause the pacemaker to detect a ventricular diastolic event from a motion signal produced by the motion sensor; start an atrial refractory period having an expiration time set based on a time of the detection of the ventricular diastolic event; detect an atrial systolic event from the motion signal after expiration of the atrial refractory period; and control a pulse generator of the pacemaker to deliver a pacing pulse to a ventricle of a patient's heart at an atrioventricular pacing time interval after the atrial systolic event detection.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

Figure 1:
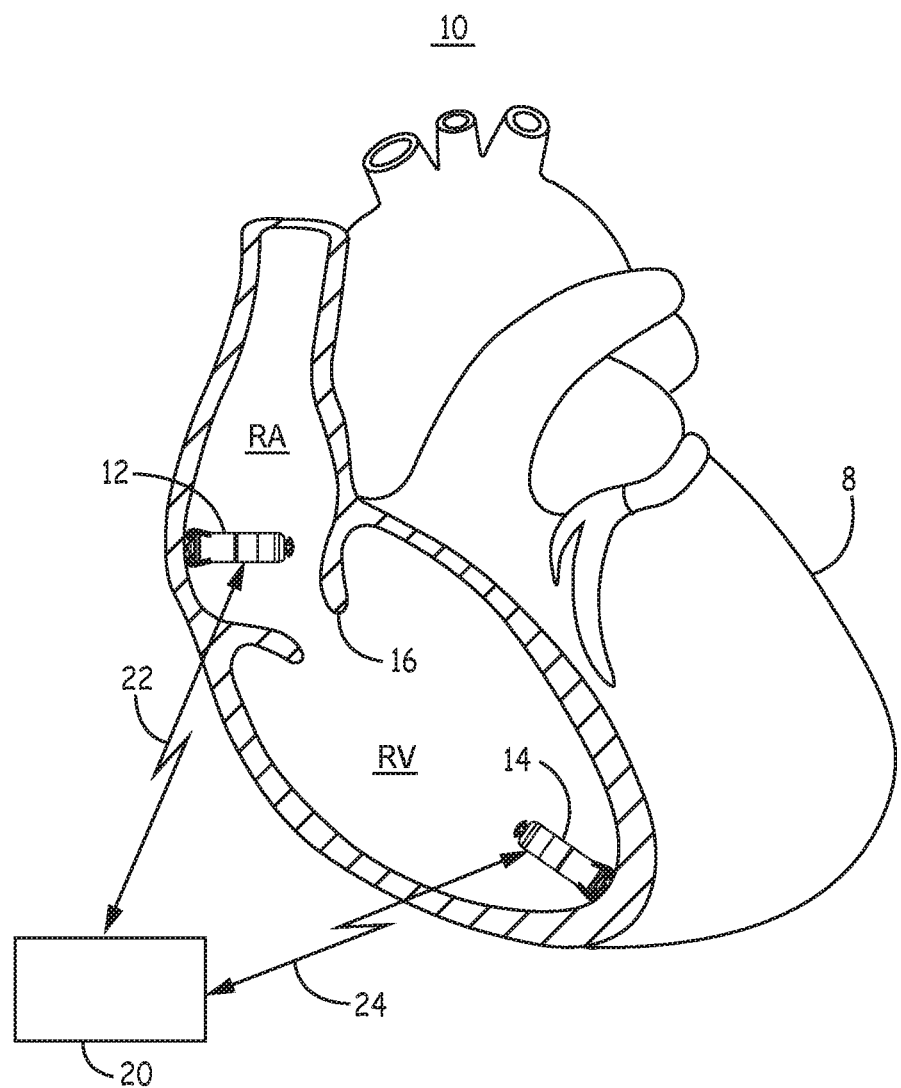
FIG. 1 is a conceptual diagram illustrating an intracardiac pacing system that may be used to sense cardiac electrical signals and motion signals induced by cardiac motion and flowing blood and provide pacing therapy to a patient's heart.

FIG. 1 is a conceptual diagram illustrating an intracardiac pacing system 10 that may be used to sense cardiac electrical signals and motion signals induced by cardiac motion and flowing blood and provide pacing therapy to a patient's heart 8. IMD system 10 includes a right ventricular (RV) intracardiac pacemaker 14 and may optionally include a right atrial (RA) intracardiac pacemaker 12 in some examples. Pacemakers 12 and 14 are transcatheter intracardiac pacemakers which may be adapted for implantation wholly within a heart chamber, e.g., wholly within the RV, wholly within the left ventricle (LV), wholly within the RA or wholly within the left atrium (LA) of heart 8.

In the example of FIG. 1, pacemaker 12 is positioned along an endocardial wall of the RA, e.g., along the RA lateral wall or RA septum. Pacemaker 14 is positioned along an endocardial wall of the RV, e.g., near the RV apex though other locations are possible. The techniques disclosed herein are not limited to the pacemaker locations shown in the example of FIG. 1 and other positions and relative locations in the heart 8 and from each other are possible. For example, a ventricular intracardiac pacemaker 14 may be positioned in the LV for and configured to detect cardiac motion signals and deliver atrial-synchronized ventricular pacing to the LV using the techniques disclosed herein.

Pacemakers 12 and 14 are reduced in size compared to subcutaneously implanted pacemakers and may be generally cylindrical in shape to enable transvenous implantation via a delivery catheter. In other examples, pacemakers 12 and 14 may be positioned at any other location inside heart 8. For example, pacemaker 12 may be positioned outside or within the right atrium or left atrium to provide respective right atrial or left atrial pacing. Pacemaker 14 may be positioned within the right ventricle or left ventricle to provide respective right ventricular or left ventricular pacing and for sensing motion signals by a motion sensor within the ventricular chamber.

Pacemakers 12 and 14 are each capable of producing electrical stimulation pulses, e.g., pacing pulses, delivered to heart 8 via one or more electrodes on the outer housing of the pacemaker. RA pacemaker 12 is configured to sense a cardiac electrical signal from within the RA that may be used to produce an RA intracardiac electrogram (EGM) signal. RV pacemaker 14 is configured to deliver RV pacing pulses and sense an RV cardiac electrical signal using housing based electrodes for producing an RV EGM signal. The cardiac electrical signals may be sensed by the respective pacemaker 12 or 14 using the housing based electrodes that are also used to deliver pacing pulses to the respective RA or RV.

In some examples, a patient may only require RV pacemaker 14 for delivering ventricular pacing. In other examples, depending on individual patient need, RA pacemaker 12 may be required for delivering atrial pacing. The RV pacemaker 14 is configured to control the delivery of ventricular pacing pulses to the RV in a manner that promotes synchrony between the RA activation and the RV activation, e.g., by maintaining a target atrioventricular (AV) interval between atrial events and ventricular pacing pulses. That is, the RV pacemaker 14 controls RV pacing pulse delivery to maintain a desired AV interval between atrial activations (intrinsic or pacing-evoked) corresponding to atrial systole and ventricular pacing pulses delivered to cause ventricular depolarization.

According to the techniques described herein, atrial activations are detected by RV pacemaker 14 from a motion sensor signal that includes motion signals caused by ventricular and atrial events. For example, acceleration of blood flowing into the RV through the tricuspid valve 16 between the RA and RV caused by atrial activation, sometimes referred to as the "atrial kick," is detected by RV pacemaker 14 from the signal produced by a motion sensor, for example an accelerometer, included in RV pacemaker 14. Other motion signals detected by RV pacemaker 14, such as motion caused by ventricular contraction, motion caused by ventricular relaxation, and motion caused by passive filling of the ventricle are described below in conjunction with FIG. 4.

Atrial P-waves that are attendant to atrial depolarization are relatively low amplitude signals in the near-field RV cardiac electrical signal received by pacemaker 14 (e.g., compared to the near-field R-wave) and therefore can be difficult to reliably detect from the cardiac electrical signal acquired by RV pacemaker 14. As such, atrial-synchronized ventricular pacing by RV pacemaker 14 may not be reliable when based solely on a cardiac electrical signal received by RV pacemaker 14. According to the techniques disclosed herein, the RV pacemaker 14 includes a motion sensor, such as an accelerometer, and is configured to detect an atrial event corresponding to atrial mechanical activation or atrial systole using a signal from the motion sensor. Ventricular pacing pulses are synchronized to the atrial event that is detected from the accelerometer signal by setting a programmable atrioventricular (AV) pacing interval that controls the timing of the ventricular pacing pulse relative to the detected atrial systolic event. As described below, detection of the atrial systolic event used to synchronize ventricular pacing pulses to atrial systole may include detection of other cardiac event motion signals in order to positively identify the atrial systolic event.

A target AV interval may be a programmed value selected by a clinician and is the time interval from the detection of the atrial event until delivery of the ventricular pacing pulse. In some instances, the target AV interval may be started from the time the atrial systolic event is detected based on a motion sensor signal or starting from an identified fiducial point of the atrial event signal. The target AV interval may be identified as being hemodynamically optimal for a given patient based on clinical testing or assessments of the patient or based on clinical data from a population of patients. The target AV interval may be determined to be optimal based on relative timing of electrical and mechanical events as identified from the cardiac electrical signal received by RV pacemaker 14 and the motion sensor signal received by RV pacemaker 14.

Pacemakers 12 and 14 may each be capable of bidirectional wireless communication with an external device 20 for programming the AV pacing interval and other pacing control parameters as well as mechanical event sensing parameters utilized for detecting ventricular mechanical events and the atrial systolic event from the motion sensor signal. Aspects of external device 20 may generally correspond to the external programming/monitoring unit disclosed in U.S. Pat. No. 5,507,782 (Kieval, et al.), hereby incorporated herein by reference in its entirety. External device 20 is often referred to as a "programmer" because it is typically used by a physician, technician, nurse, clinician or other qualified user for programming operating parameters in pacemakers 12 and 14. External device 20 may be located in a clinic, hospital or other medical facility. External device 20 may alternatively be embodied as a home monitor or a handheld device that may be used in a medical facility, in the patient's home, or another location. Operating parameters, including sensing and therapy delivery control parameters, may be programmed into pacemakers 12 and 14 using external device 20.

External device 20 is configured for bidirectional communication with implantable telemetry circuitry included in RV pacemaker 14 and RA pacemaker 12 (when present). External device 20 establishes a wireless radio frequency (RF) communication link 22 with RA pacemaker 12 and wireless RF communication link 24 with RV pacemaker 14 using a communication protocol that appropriately addresses the targeted pacemaker 12 or 14. Communication links 22 and 24 may be established using an RF link such as BLUETOOTH®, Wi-Fi, Medical Implant Communication Service (MICS) or other communication bandwidth. In some examples, external device 20 may include a programming head that is placed proximate pacemaker 12 or 14 to establish and maintain a communication link, and in other examples external device 20 and pacemakers 12 and 14 may be configured to communicate using a distance telemetry algorithm and circuitry that does not require the use of a programming head and does not require user intervention to maintain a communication link. An example RF telemetry communication system that may be implemented in system 10 is generally disclosed in U.S. Pat. No. 5,683,432 (Goedeke, et al.), hereby incorporated herein by reference in its entirety.

External device 20 may display data and information relating to pacemaker functions to a user for reviewing pacemaker operation and programmed parameters as well as EGM signals transmitted from pacemaker 14 or pacemaker 12, motion sensor signals acquired by pacemaker 14, or other physiological data that is acquired by and retrieved from pacemakers 12 and/or 14 during an interrogation session.

It is contemplated that external device 20 may be in wired or wireless connection to a communications network via a telemetry circuit that includes a transceiver and antenna or via a hardwired communication line for transferring data to a remote database or computer to allow remote management of the patient. Remote patient management systems including a remote patient database may be configured to utilize the presently disclosed techniques to enable a clinician to review EGM, motion sensor, and marker channel data and authorize programming of sensing and therapy control parameters in RV pacemaker 14, e.g., after viewing a visual representation of EGM, motion sensor signal and marker channel data.

Pacemaker 12 and pacemaker 14 may or may not be configured to communicate directly with each other. When pacemakers 12 and 14 are configured to communicate with each other, communication may be minimized in order to conserve battery life of the intracardiac pacemakers 12 and 14. As such, communication may not occur on a beat-by-beat basis between the RA pacemaker 12 and RV pacemaker 14 for communicating when the other pacemaker is sensing cardiac events or when it is delivering pacing pulses. As disclosed herein, RV pacemaker 14, however, is configured to detect atrial events as often as beat-by-beat from a motion sensor signal, without requiring communication signals from RA pacemaker 12 to provide atrial event detection for controlling atrial-synchronized ventricular pacing.

Figure 2A:
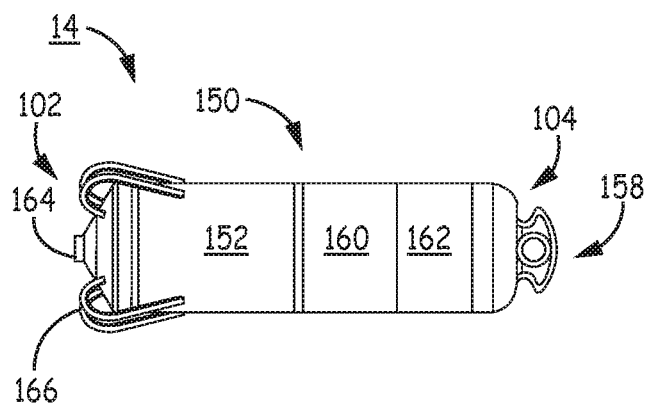
FIG. 2A is a conceptual diagram of the intracardiac ventricular pacemaker shown in FIG. 1.

FIG. 2A is a conceptual diagram of the intracardiac RV pacemaker 14 shown in FIG. 1. RV pacemaker 14 includes electrodes 162 and 164 spaced apart along the housing 150 of pacemaker 14 for sensing cardiac electrical signals and delivering pacing pulses. Electrode 164 is shown as a tip electrode extending from a distal end 102 of pacemaker 14, and electrode 162 is shown as a ring electrode along a mid-portion of housing 150, for example adjacent proximal end 104. Distal end 102 is referred to as "distal" in that it is expected to be the leading end as pacemaker 14 is advanced through a delivery tool, such as a catheter, and placed against a targeted pacing site.

Electrodes 162 and 164 form an anode and cathode pair for bipolar cardiac pacing and sensing. In alternative embodiments, pacemaker 14 may include two or more ring electrodes, two tip electrodes, and/or other types of electrodes exposed along pacemaker housing 150 for delivering electrical stimulation to heart 8 and sensing cardiac electrical signals. Electrodes 162 and 164 may be, without limitation, titanium, platinum, iridium or alloys thereof and may include a low polarizing coating, such as titanium nitride, iridium oxide, ruthenium oxide, platinum black among others. Electrodes 162 and 164 may be positioned at locations along pacemaker 14 other than the locations shown.

Housing 150 is formed from a biocompatible material, such as a stainless steel or titanium alloy. In some examples, the housing 150 may include an insulating coating. Examples of insulating coatings include parylene, urethane, PEEK, or polyimide among others. The entirety of the housing 150 may be insulated, but only electrodes 162 and 164 uninsulated. Electrode 164 may serve as a cathode electrode and be coupled to internal circuitry, e.g., a pacing pulse generator and cardiac electrical signal sensing circuitry, enclosed by housing 150 via an electrical feedthrough crossing housing 150. Electrode 162 may be formed as a conductive portion of housing 150 as a ring electrode that is electrically isolated from the other portions of the housing 150 as generally shown in FIG. 2A. In other examples, the entire periphery of the housing 150 may function as an electrode that is electrically isolated from tip electrode 164, instead of providing a localized ring electrode such as anode electrode 162. Electrode 162 formed along an electrically conductive portion of housing 150 serves as a return anode during pacing and sensing.

The housing 150 includes a control electronics subassembly 152, which houses the electronics for sensing cardiac signals, producing pacing pulses and controlling therapy delivery and other functions of pacemaker 14 as described below in conjunction with FIG. 3. A motion sensor may be implemented as an accelerometer enclosed within housing 150 in some examples. The accelerometer provides a signal to a processor included in control electronics subassembly 152 for signal processing and analysis for detecting ventricular mechanical events and atrial systolic events for timing ventricular pacing pulses as described below.

Housing 150 further includes a battery subassembly 160, which provides power to the control electronics subassembly 152. Battery subassembly 160 may include features of the batteries disclosed in commonly-assigned U.S. Pat. No. 8,433,409 (Johnson, et al.) and U.S. Pat. No. 8,541,131 (Lund, et al.), both of which are hereby incorporated by reference herein in their entirety.

Pacemaker 14 may include a set of fixation tines 166 to secure pacemaker 14 to patient tissue, e.g., by actively engaging with the ventricular endocardium and/or interacting with the ventricular trabeculae. Fixation tines 166 are configured to anchor pacemaker 14 to position electrode 164 in operative proximity to a targeted tissue for delivering therapeutic electrical stimulation pulses. Numerous types of active and/or passive fixation members may be employed for anchoring or stabilizing pacemaker 14 in an implant position. Pacemaker 14 may include a set of fixation tines as disclosed in commonly-assigned, pre-grant publication U.S. 2012/0172892 (Grubac, et al.), hereby incorporated herein by reference in its entirety.

Pacemaker 14 may optionally include a delivery tool interface 158. Delivery tool interface 158 may be located at the proximal end 104 of pacemaker 14 and is configured to connect to a delivery device, such as a catheter, used to position pacemaker 14 at an implant location during an implantation procedure, for example within a heart chamber.

Figure 2B:
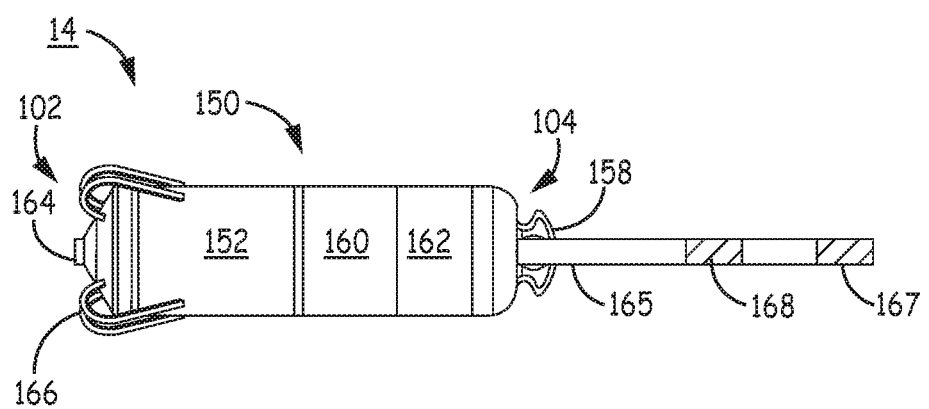
FIG. 2B is a conceptual diagram of another example of the intracardiac ventricular pacemaker shown in FIG. 1.

FIG. 2B is a conceptual diagram of another example of RV pacemaker 14. In FIG. 2B, RV pacemaker 14 includes a proximal sensing extension 165 extending away from housing 150 and carrying a pair of sensing electrodes 167 and 168. The proximal sensing extension 165 may be coupled to the housing 150 for positioning a return sensing electrode 168 or 167 which may be paired with distal electrode 164 at an increased inter-electrode distance compared to the inter-electrode spacing of housing-based electrodes 162 and 164. The increased inter-electrode distance may facilitate sensing of far-field atrial signals such as P-waves attendant to atrial depolarization.

Alternatively, electrodes 167 and 168 may form a sensing electrode pair for sensing atrial P-waves. When distal end 102 is fixed along the RV apex, sensing extension 165 may extend toward the RA thereby positioning electrodes 167 and 168 nearer the atrial tissue for sensing far-field atrial P-waves. One electrode 167 may be coupled to sensing circuitry enclosed in housing 150 via an electrical feedthrough crossing housing 150, and one electrode 168 may be coupled to housing 150 to serve as a ground electrode.

Figure 3:
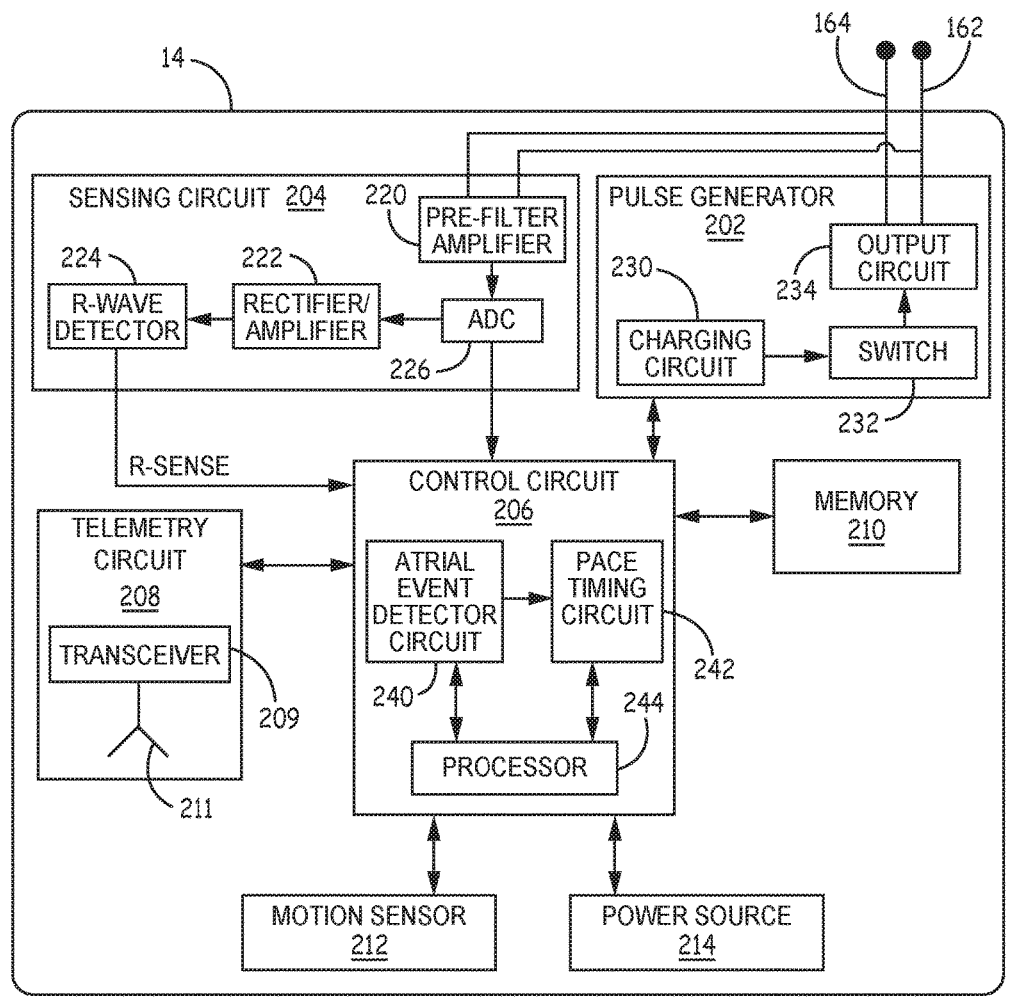
FIG. 3 is a schematic diagram of an example configuration of the pacemaker of FIG. 2A.

FIG. 3 is a schematic diagram of an example configuration of pacemaker 14 shown in FIG. 1. Pacemaker 14 includes a pulse generator 202, a sensing circuit 204, a control circuit 206, memory 210, telemetry circuit 208, motion sensor 212 and a power source 214. Motion sensor 212 is implemented as an accelerometer in the examples described herein and may also be referred to herein as "accelerometer 212." Motion sensor 212 is not limited to being an accelerometer, however, and other motion sensors may be utilized successfully in pacemaker 14 for detecting cardiac motion signals according to the techniques described herein. Examples of motion sensors that may be implemented in pacemaker 14 include piezoelectric sensors and micro electro-mechanical systems (MEMS) devices.

Motion sensor 212 may be a multi-axis sensor, e.g., a two-dimensional or three-dimensional sensor, with each axis providing a signal that may be analyzed individually or in combination for detecting cardiac mechanical events. Motion sensor 212 produces an electrical signal correlated to motion or vibration of sensor 212 (and pacemaker 14), e.g., when subjected to flowing blood and cardiac motion. Motion sensor 212 may be a one-dimensional, single axis accelerometer, two-dimensional or three-dimensional multi-axis accelerometer. One example of an accelerometer for use in implantable medical devices is generally disclosed in U.S. Pat. No. 5,885,471 (Ruben, et al.), incorporated herein by reference in its entirety. An implantable medical device arrangement including a piezoelectric accelerometer for detecting patient motion is disclosed, for example, in U.S. Pat. No. 4,485,813 (Anderson, et al.) and U.S. Pat. No. 5,052,388 (Sivula, et al.), both of which patents are hereby incorporated by reference herein in their entirety. Examples of three-dimensional accelerometers that may be implemented in pacemaker 14 and used for detecting cardiac mechanical events using the presently disclosed techniques are generally described in U.S. Pat. No. 5,593,431 (Sheldon) and U.S. Pat. No. 6,044,297 (Sheldon), both of which are incorporated herein by reference in their entirety. Other accelerometer designs may be used for producing an electrical signal that is correlated to motion imparted on pacemaker 14 due to ventricular and atrial events.

The various circuits represented in FIG. 3 may be combined on one or more integrated circuit boards which include a specific integrated circuit (ASIC), an electronic circuit, a processor (shared, dedicated, or group) and memory that execute one or more software or firmware programs, a combinational logic circuit, state machine or other suitable components that provide the described functionality.

Sensing circuit 204 is configured to receive a cardiac electrical signal via electrodes 162 and 164 by a pre-filter and amplifier circuit 220. Pre-filter and amplifier circuit may include a high pass filter to remove DC offset, e.g., a 2.5 to 5 Hz high pass filter, or a wideband filter having a passband of 2.5 Hz to 100 Hz to remove DC offset and high frequency noise. Pre-filter and amplifier circuit 220 may further include an amplifier to amplify the "raw" cardiac electrical signal passed to analog-to-digital converter (ADC) 226. ADC 226 may pass a multi-bit, digital electrogram (EGM) signal to control circuit 206 for use by atrial event detector circuit 240 in identifying ventricular electrical events (e.g., R-waves or T-waves) and/or atrial electrical events, e.g., P-waves. Identification of cardiac electrical events may be used in algorithms for detecting atrial systolic events from the motion sensor signal. The digital signal from ADC 226 may be passed to rectifier and amplifier circuit 222, which may include a rectifier, bandpass filter, and amplifier for passing a cardiac signal to R-wave detector 224.

R-wave detector 224 may include a sense amplifier or other detection circuitry that compares the incoming rectified, cardiac electrical signal to an R-wave detection threshold, which may be an auto-adjusting threshold. When the incoming signal crosses the R-wave detection threshold, the R-wave detector 224 produces an R-wave sensed event signal (R-sense) that is passed to control circuit 206. In other examples, R-wave detector 224 may receive the digital output of ADC 226 for detecting R-waves by a comparator, morphological signal analysis of the digital EGM signal or other R-wave detection techniques. R-wave sensed event signals passed from R-wave detector 224 to control circuit 206 may be used for scheduling ventricular pacing pulses by pace timing circuit 242 and for use in identifying the timing of ventricular electrical events in algorithms performed by atrial event detector circuit 240 for detecting atrial systolic events from a signal received from motion sensor 212.

Control circuit 206 includes an atrial event detector circuit 240, pace timing circuit 242, and processor 244. Atrial event detector circuit 240 is configured to detect atrial mechanical events from a signal received from motion sensor 212. As described below, one or more ventricular mechanical events may be detected from the motion sensor signal in a given cardiac cycle to facilitate positive detection of the atrial systolic event from the motion sensor signal during the ventricular cycle.

Control circuit 206 may receive R-wave sensed event signals and/or digital cardiac electrical signals from sensing circuit 204 for use in detecting and confirming cardiac events and controlling ventricular pacing. For example, R-wave sensed event signals may be passed to pace timing circuit 242 for inhibiting scheduled ventricular pacing pulses or scheduling ventricular pacing pulses when pacemaker 14 is operating in a non-atrial tracking ventricular pacing mode. R-wave sensed event signals may also be passed to atrial event detector circuit 240 for use in setting ventricular event detection windows and/or atrial event refractory periods, for example as shown and described in conjunction with FIG. 6.

Atrial event detector circuit 240 receives a motion signal from motion sensor 212 and starts an atrial refractory period in response to a ventricular electrical event, e.g., an R-wave sensed event signal from sensing circuit 204 or delivery of a pacing pulse by pulse generator 202. Atrial event detector circuit 240 determines if the motion sensor signal satisfies atrial mechanical event detection criteria outside of the refractory period. The motion sensor signal during the refractory period may be monitored by atrial event detector circuit 240 for the purposes of detecting ventricular mechanical events, which may be used for confirming or validating atrial systolic event detection and/or setting atrial systolic event detection control parameters as further described below, e.g., in conjunction with FIG. 10. As such, ventricular mechanical event detection windows may be set during the atrial refractory period and may be set according to predetermined time intervals following identification of a ventricular electrical event. Atrial event detector circuit 240 may be configured to detect one or more ventricular mechanical events during respective ventricular event detection windows during the atrial refractory period. The timing and detection of the ventricular mechanical events may be used to update the atrial refractory period and/or an atrial systolic detection threshold amplitude and may be used to confirm detection of the atrial systolic event occurring subsequent to expected ventricular mechanical events.

Atrial event detector circuit 240 passes an atrial event detection signal to processor 244 and/or pace timing circuit 242. Pace timing circuit 242 (or processor 244) may additionally receive R-wave sensed event signals from R-wave detector 224 for use in controlling the timing of pacing pulses delivered by pulse generator 202. Processor 244 may include one or more clocks for generating clock signals that are used by pace timing circuit 242 to time out an AV pacing interval that is started upon receipt of an atrial event detection signal from atrial event detector circuit 240. Pace timing circuit 242 may include one or more pacing escape interval timers or counters that are used to time out the AV pacing interval, which may be a programmable interval stored in memory 210 and retrieved by processor 244 for use in setting the AV pacing interval used by pace timing circuit 242.

Pace timing circuit 242 may additionally include a lower pacing rate interval timer for controlling a minimum ventricular pacing rate. For example, if an atrial systolic event is not detected from the motion sensor signal triggering a ventricular pacing pulse at the programmed AV pacing interval, a ventricular pacing pulse may be delivered by pulse generator 202 upon expiration of the lower pacing rate interval to prevent ventricular asystole and maintain a minimum ventricular rate.

Processor 244 may retrieve other programmable pacing control parameters, such as pacing pulse amplitude and pacing pulse width that are passed to pulse generator 202 for controlling pacing pulse delivery. In addition to providing control signals to pace timing circuit 242 and pulse generator 202 for controlling pacing pulse delivery, processor 244 may provide sensing control signals to sensing circuit 204, e.g., R-wave sensing threshold, sensitivity, various blanking and refractory intervals applied to the cardiac electrical signal, and atrial event detection control signals to atrial event detector circuit 240 for use in detecting and confirming atrial systolic events, e.g., ventricular event detection windows, atrial refractory period, detection threshold amplitudes applied to the motion sensor signal, and any other atrial event detection criteria applied by circuitry included in atrial event detector circuit 240.

The functions attributed to pacemaker 14 herein may be embodied as one or more processors, controllers, hardware, firmware, software, or any combination thereof. Depiction of different features as specific circuitry is intended to highlight different functional aspects and does not necessarily imply that such functions must be realized by separate hardware, firmware or software components or by any particular circuit architecture. Rather, functionality associated with one or more circuits described herein may be performed by separate hardware, firmware or software components, or integrated within common hardware, firmware or software components. For example, atrial systolic event detection from the motion sensor signal and ventricular pacing control operations performed by pacemaker 14 may be implemented in control circuit 206 executing instructions stored in memory 210 and relying on input from sensing circuit 204 and motion sensor 212.

The operation of circuitry included in pacemaker 14 as disclosed herein should not be construed as reflective of a specific form of hardware, firmware and software necessary to practice the techniques described. It is believed that the particular form of software, hardware and/or firmware will be determined primarily by the particular system architecture employed in the pacemaker 14 and by the particular sensing and therapy delivery circuitry employed by the pacemaker 14. Providing software, hardware, and/or firmware to accomplish the described functionality in the context of any modern pacemaker, given the disclosure herein, is within the abilities of one of skill in the art.

Pulse generator 202 generates electrical pacing pulses that are delivered to the RV of the patient's heart via cathode electrode 164 and return anode electrode 162. Pulse generator 202 may include charging circuit 230, switching circuit 232 and an output circuit 234 Charging circuit 230 may include a holding capacitor that may be charged to a pacing pulse amplitude by a multiple of the battery voltage signal of power source 214 under the control of a voltage regulator. The pacing pulse amplitude may be set based on a control signal from control circuit 206. Switching circuit 232 may control when the holding capacitor of charging circuit 230 is coupled to the output circuit 234 for delivering the pacing pulse. For example, switching circuit 232 may include a switch that is activated by a timing signal received from pace timing circuit 242 upon expiration of an AV pacing interval (or lower rate pacing interval) and kept closed for a programmed pacing pulse duration to enable discharging of the holding capacitor of charging circuit 230. The holding capacitor, previously charged to the pacing pulse voltage amplitude, is discharged across electrodes 162 and 164 through the output capacitor of output circuit 234 for the programmed pacing pulse duration. Examples of pacing circuitry generally disclosed in U.S. Pat. No. 5,507,782 (Kieval, et al.) and in commonly assigned U.S. Pat. No. 8,532,785 (Crutchfield, et al.), both of which patents are incorporated herein by reference in their entirety, may be implemented in pacemaker 14 for charging a pacing capacitor to a predetermined pacing pulse amplitude under the control of control circuit 206 and delivering a pacing pulse.

Memory 210 may include computer-readable instructions that, when executed by control circuit 206, cause control circuit 206 to perform various functions attributed throughout this disclosure to pacemaker 14. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal. Memory 210 may store timing intervals and other data used by control circuit 206 to control the delivery of pacing pulses by pulse generator 202, e.g., by detecting an atrial systolic event by atrial event detector circuit 240 from the motion sensor signal and setting a pacing escape interval timer included in pace timing circuit 242, according to the techniques disclosed herein.

Power source 214 provides power to each of the other circuits and components of pacemaker 14 as required. Control circuit 206 may execute power control operations to control when various circuits or components are powered to perform various pacemaker functions. Power source 214 may include one or more energy storage devices, such as one or more rechargeable or non-rechargeable batteries. The connections between power source 214 and other pacemaker circuits and components are not shown in FIG. 3 for the sake of clarity.

Telemetry circuit 208 includes a transceiver 209 and antenna 211 for transferring and receiving data via a radio frequency (RF) communication link. Telemetry circuit 208 may be capable of bi-directional communication with external device 20 (FIG. 1) as described above. Motion sensor signals and cardiac electrical signals, and/or data derived therefrom may be transmitted by telemetry circuit 208 to external device 20. Programmable control parameters and algorithms for performing atrial event detection and ventricular pacing control may be received by telemetry circuit 208 and stored in memory 210 for access by control circuit 206.

Figure 4:
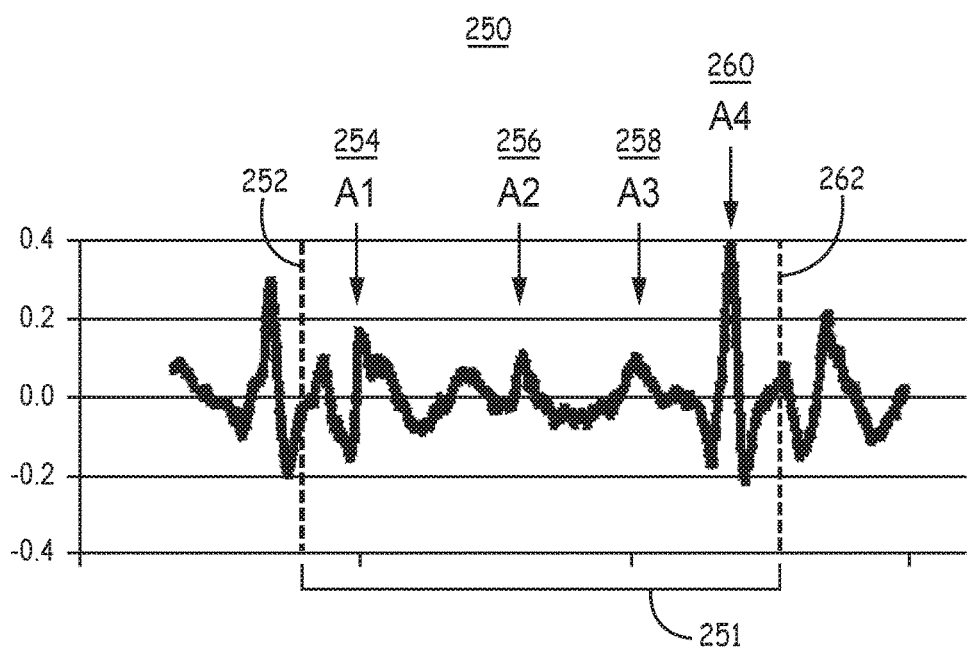
FIG. 4 is an example of a motion sensor signal that may be acquired over a cardiac cycle by a motion sensor included in the ventricular intracardiac pacemaker of FIG. 1.

FIG. 4 is an example of a motion sensor signal 250 that may be acquired by motion sensor 212 over a cardiac cycle. Vertical dashed lines 252 and 262 denote the timing of two consecutive ventricular events (an intrinsic ventricular depolarization or a ventricular pace), marking the respective beginning and end of the ventricular cycle 251. The motion signal includes an A1 event 254, an A2 event 256, an A3 event 258 and an A4 event 260. The A1 event 254 is an acceleration signal (in this example when motion sensor 250 is implemented as an accelerometer) that occurs during ventricular contraction and marks the approximate onset of ventricular mechanical systole. The A1 event is also referred to herein as a "ventricular contraction event." The A2 event 265 is an acceleration signal that occurs during ventricular relaxation and marks the approximate offset or end of ventricular mechanical systole. The A2 event is also referred to herein as the "ventricular relaxation event." The A3 event 258 is an acceleration signal that occurs during passive ventricular filling and marks ventricular mechanical diastole. The A3 event is also referred to herein as the "ventricular passive filling event." Since the A2 event occurs with the end of ventricular systole, it is an indicator of the onset of ventricular diastole. The A3 event occurs during ventricular diastole. As such, the A2 and A3 events may be collectively referred to as ventricular mechanical diastolic events because they are both indicators of the ventricular diastolic period.

The A4 event 260 is an acceleration signal that occurs during atrial contraction and active ventricular filling and marks atrial mechanical systole. The A4 event 260 is also referred to herein as the "atrial systolic event" or merely the "atrial event," and is the atrial systolic event that is detected from motion sensor signal 250 by atrial event detector circuit 240 for controlling pace timing circuit 242 to trigger ventricular pacing pulse delivery by starting an AV pacing interval in response to detecting the A4 event 260. As described below, control circuit 206 may be configured to detect one or more of the A1, A2, and A3 events from motion sensor signal 250, for at least some ventricular cardiac cycles, for use in positively detecting the A4 event 260 and setting atrial event detection control parameters. The A1, A2 and/or A3 events may be detected and characterized to avoid false detection of A4 events and promote reliable A4 event detection for proper timing of atrial-synchronized ventricular pacing pulses.

Figure 5:
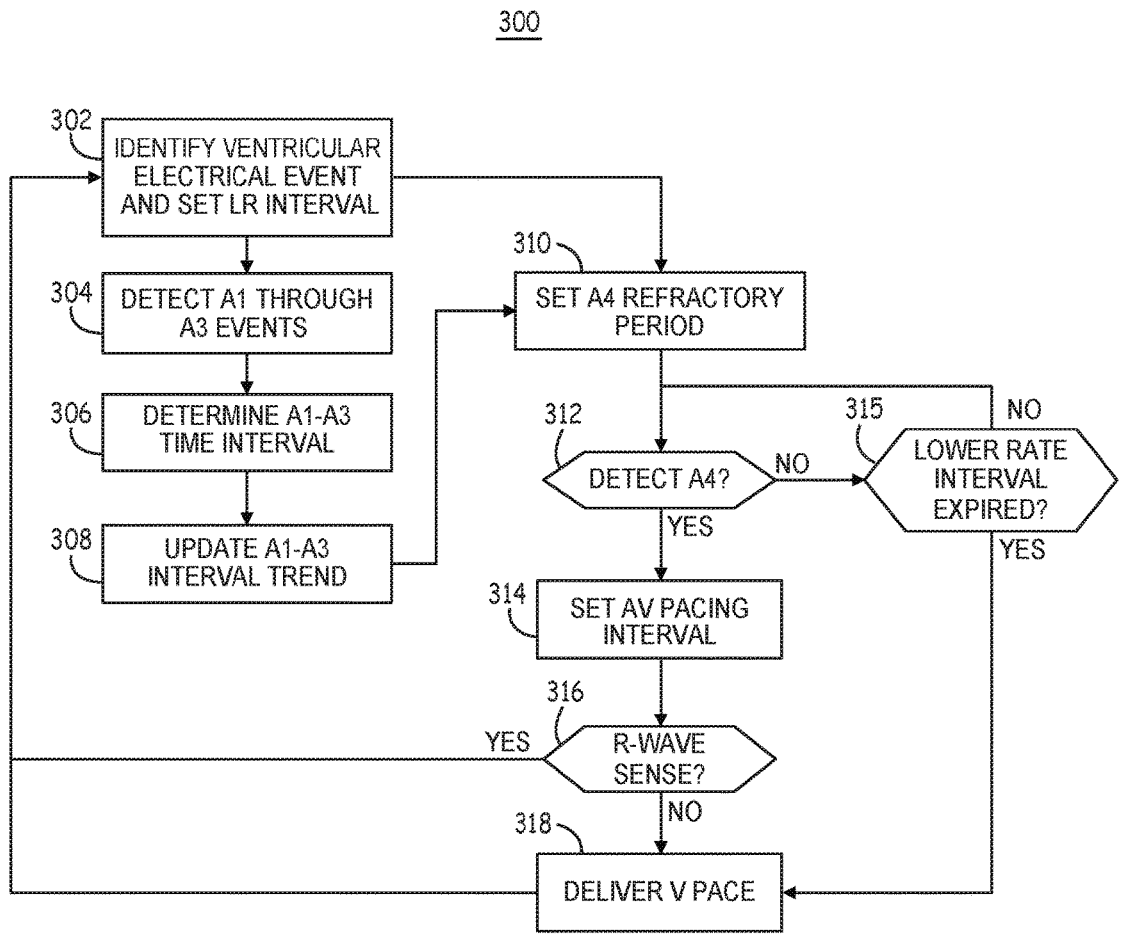
FIG. 5 is a flow chart of one method performed by an intracardiac ventricular pacemaker for detecting an atrial systolic event from a motion sensor signal and controlling ventricular pacing.

FIG. 5 is a flow chart 300 of one method performed by pacemaker 14 for detecting the A4 event and controlling ventricular pacing. At block 302, control circuit 206 identifies a ventricular event. The ventricular event may be an R-wave sensed event signal received from sensing circuit 204 or a ventricular pacing pulse delivered by pulse generator 202. Since the ventricular A1, A2 and A3 events may have different characteristics during an intrinsic ventricular rhythm than during a ventricular paced rhythm, the methods described herein for determining amplitudes, time intervals or other characteristics of the A1, A2 and A3 events for use in setting A4 detection control parameters or confirming A4 event detection may be determined for both an intrinsic ventricular rhythm and a ventricular paced rhythm.

For example, as described in conjunction with the flow charts and timing diagrams presented herein, various time intervals, sensing windows, atrial refractory period, and atrial event detection threshold amplitude may be set based on characterizations of one or more of the A1, A2 and A3 events. One set of A4 detection control parameters and characteristics of the A1, A2 and A3 events may be determined and stored for use during episodes of ventricular sensing (ventricular intrinsic rhythm), and another set of A4 detection control parameters and characteristics of the A1, A2 and A3 events may be determined and stored for used during episodes of ventricular pacing.

During ventricular sensing, control circuit 206 may be configured to discriminate a normal sinus R-wave from a premature ventricular contraction (PVC) so that ventricular events identified at block 302 for use in starting a search for the A1 through A4 events from the motion sensor signal do not include PVCs. When a ventricular event, sensed or paced, is identified at block 302 that is not a PVC, pace timing circuit 242 may set an escape interval timer to a lower rate (LR) pacing interval. If the lower rate pacing interval expires (as described below in conjunction with block 315), a ventricular pacing pulse may be delivered, asynchronous to atrial activity, in order to maintain some minimum, base ventricular rate.

At block 304, atrial event detector 240 detects the A1 through A3 motion signals. Briefly, atrial event detector 240 may compare the motion sensor signal to one or more pre-determined detection threshold amplitudes during one or more time windows set in response to identifying the ventricular event at bock 302 for detecting the A1 through A3 events. In some examples, the A4 event may also be detected at block 304 to increase confidence in the positive identification of each of the four motion sensor signals A1 through A4 in a given cardiac cycle. In this example, the A1 through A3 events, and optionally A4, may be detected on a beat-by-beat basis.

After the A1 through A3 events are detected, the A1-A3 time interval is determined at block 304 as the time interval from the A1 event detection to the A3 event detection. The A1-A3 time interval may be used to update an A1-A3 interval trend at block 308. For example, a running average A1-A3 time interval may be updated at block 308 using the most recent N A1-A3 time interval measurements, e.g., the most recent three to twelve A1-A3 time intervals.

The A1-A3 time interval is used to set a post-ventricular atrial refractory period at block 310. This atrial refractory period is also referred to herein as an "A4 refractory period" because A4 event detection is inhibited during the atrial refractory period. When a ventricular event is identified at block 302, atrial event detector 240 may start the atrial refractory period at block 310. The atrial refractory period may be set to a percentage longer than or a fixed interval longer than the A1-A3 time interval. For example, the atrial refractory period may be set to be 50 to 150 ms longer than the A1-A3 time interval, though shorter or longer fixed intervals may be added to the A1-A3 time interval for setting the atrial refractory period. The fixed time interval used to set the atrial refractory period may vary depending on heart rate in some examples.

During the atrial refractory period, any motion sensor events that are detected, or cross a detection threshold amplitude, are ignored for the purposes of triggering a ventricular pacing pulse and starting an AV pacing interval. Ventricular mechanical events A1 through A3 may be detected during the atrial refractory period, as indicated at block 304, to determine the A1-A3 time interval and update the A1-A3 interval trend (blocks 306 and 308), either periodically or on a beat-by-beat basis.

At block 312, atrial event detector circuit 240 monitors the motion sensor signal to detect the A4 event after the expiration of the atrial refractory period. If the A4 event is not detected before the lower pacing rate interval expires (block 315), a ventricular pacing pulse is delivered at block 316 to ensure a minimum ventricular rate, e.g., 40 to 60 beats per minute. Furthermore, it is to be understood that if an intrinsic R-wave is sensed before an A4 event is detected, the process of FIG. 5 may return to block 302 where the sensed R-wave is identified as a ventricular electrical event and control circuit 206 restarts the process of detecting the A4 event on the next ventricular cycle.

If the A4 event is detected before the lower pacing rate interval expires, control circuit 206 sets the AV pacing interval at block 314 in response to detecting the A4 event. If an intrinsic R-wave is not sensed from the cardiac electrical signal by sensing circuit 204 during the AV pacing interval, "no" branch of block 316, a ventricular pacing pulse is delivered by pulse generator 202 at block 318 upon expiration of the AV pacing interval. The ventricular pacing pulse, if delivered, and otherwise the sensed R-wave, is identified as the next ventricular event at block 302 and the process repeats.

In this way, the A1 through A3 events may be detected from the motion sensor signal on a beat-by-beat (or less frequent) basis for updating the A1-A3 time interval trend used to set the atrial refractory period to provide a high likelihood of positively detecting the A4 event and properly timing a ventricular pacing pulse in synchrony with the atrial event. Other motion sensor signal events A1 through A3 are unlikely to be falsely detected as the A4 event by applying the atrial refractory period set based on the A1-A3 timing.

In some examples, rather than determining an A1-A3 time interval, a time interval to the A2 event may be determined so that the atrial refractory period is set based on the A1-A2 time interval to extend through at least the A2 event and expire before the A3 event. In this example, an A4 detection threshold amplitude may be set higher than an expected A3 event amplitude to allow detection of the A4 event earlier in the ventricular cycle, for example as the atrial rate is increasing. In other cases, the time interval from the identified ventricular electrical event to the A1, A2 or A3 event may be determined and used in setting the atrial refractory period.

In some examples, the process of blocks 304 through 308 is performed periodically rather than on a beat-by-beat basis. For example detection of A1-A3 events during the atrial refractory period may occur on every third cardiac cycle, every eighth cardiac cycle, once a minute, or other predetermined schedule for updating the A1-A3 time interval (or other ventricular event time interval as discussed above) used for setting the atrial refractory period at block 310. In some cases, the heart rate, paced or intrinsic, may be monitored and the A1-A3 events may be detected for updating the A1-A3 interval trend when the heart rate changes by more than a predetermined amount. For example, ventricular event intervals between consecutive ventricular events may be determined upon identifying ventricular events at block 302. The ventricular event intervals may be RR intervals between consecutively sensed intrinsic R-waves or VV intervals between consecutively delivered ventricular pacing pulses and may include RV intervals between a sensed intrinsic R-wave and a consecutively delivered pacing pulse and VR intervals between a delivered pacing pulse and a consecutively sensed R-wave. Both the intrinsic heart rate and the paced rate may change, e.g., when pacemaker 14 is a rate responsive pacemaker. If the ventricular event interval changes or a trend in the ventricular event interval changes by more than a predetermined amount, the control circuit may perform blocks 304 through 308 to update the A1-A3 interval trend used for setting the atrial refractory period.

In other examples, if the A4 event is not detected at block 312 after the atrial refractory period and before the next ventricular event (intrinsic or paced) is identified at block 302, the control circuit 206 may perform the process of blocks 304 through 306 for a predetermined number of consecutive or non-consecutive cardiac cycles to update the A1-A3 interval trend used to set the atrial refractory period to restore A4 detection.

Figure 6:
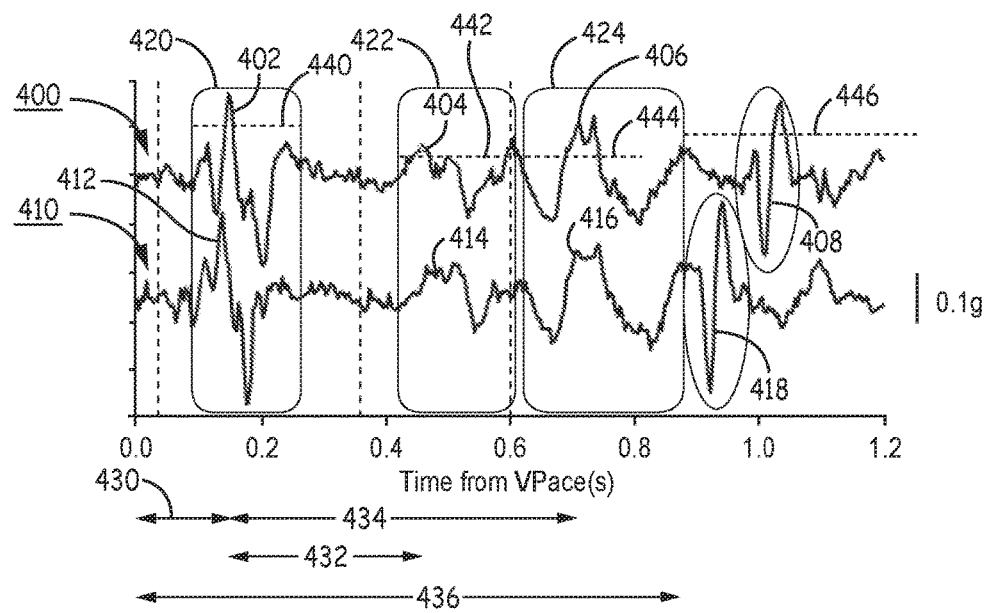
FIG. 6 is an example of a motion sensor signal acquired over two different ventricular cycles.

FIG. 6 is an example of a motion sensor signals 400 and 410 acquired over two different cardiac cycles. A ventricular pacing pulse is delivered at time 0.0 seconds for both cardiac cycles. The top sensor signal 400 is received over one cardiac cycle and the bottom sensor signal 401 is received over a different cardiac cycle. The two signals 400 and 410 are aligned in time at 0.0 seconds, the time of the ventricular pacing pulse delivery.

The A1 events 402 and 412 of the respective motion sensor signals 400 and 410, which occur during ventricular contraction, are observed to be well-aligned in time following the ventricular pacing pulse at time 0.0 seconds. Similarly, the A2 events 404 and 414 (occurring during ventricular relaxation) and the A3 events 406 and 416 (occurring during passive ventricular filling) are well-aligned in time. Since the A1, A2 and A3 events are ventricular events, occurring during ventricular contraction, ventricular relaxation, and passive ventricular filling, respectively, these events are expected to occur at relatively consistent intervals following a ventricular electrical event, the ventricular pacing pulse in this example, and relative to each other. The time relationship of the A1, A2 and A3 events may be different following a ventricular pacing pulse compared to following a sensed intrinsic R-wave, however, during a stable paced or intrinsic ventricular rhythm, the relative timing of A1, A2 and A3 events to each other and the immediately preceding ventricular electrical event is expected to be consistent.

The A4 events 408 and 418 of the first and second motion sensor signals 400 and 410 respectively are not aligned in time. The A4 event occurs during atrial systole and as such the time interval of the A4 event following the immediately preceding ventricular electrical event (sensed R-wave or ventricular pacing pulse) and the preceding A1 through A3 events may vary between cardiac cycles.

The consistency of the timing of the A1 through A3 events relative to each other and the immediately preceding ventricular electrical event may be used for determining the atrial refractory period and increasing confidence in reliably detecting A4 events 408 and 418. In some examples, an A1 sensing window 420 may be set based on an expected Vpace-A1 time interval. The Vpace-A1 time interval 430 may be measured when the motion sensor signal 400 or 410 crosses an A1 sensing threshold amplitude 440. The A1 sensing window 420 may be adjusted on the next cardiac cycle based on the Vpace-A1 time interval 430 determined on the current cardiac cycle or a running average Vpace-A1 time interval.

An A2 sensing window 422 may be set based on an expected Vpace-A2 time interval (not explicitly shown but understood to be the total time from 0.0 seconds to an A2 event detection) or an A1-A2 time interval 432 (time from A1 detection to time of A2 detection). The A2 event 404 or 414 may be detected at the time of the first positive-going crossing of an A2 sensing threshold amplitude 442 by the motion sensor signal 400 or 410 during the A2 sensing window 422. The A2 sensing window 422 may be adjusted on the next cardiac cycle based on the Vpace-A2 time interval or A1-A2 time interval 432 determined on the current cardiac cycle.

Similarly, an A3 sensing window 424 may be set based on an expected Vpace-A3 time interval (not explicitly labeled but understood to be sum of time intervals 430 and 434), A1-A3 time interval 434, or A2-A3 time interval (not explicitly labeled but understood to be the time interval from the sensed A2 event 404 or 414 to the sensed A3 event 406 or 416). The A3 event 406 or 416 may be detected during the A3 sensing window 424 when the motion sensor signal 400 or 410, respectively, crosses an A3 sensing threshold amplitude 444. The A3 sensing window 424 may be adjusted on the next cardiac cycle based on the Vpace-A3 time interval, A1-A3 time interval 434, or the A2-A3 time interval determined during the current cardiac cycle.

Each of the sensing windows 420, 422 and 424 may be set based on a history of time intervals determined from a ventricular pacing pulse or sensed intrinsic R-wave to the respective A1 event 402 or 412, A2 event 404 or 414 and A3 event 406 or 416 or based on a history of time intervals between the detected A1, A2 and A3 events or any combination thereof. For example, the A2 sensing window 422 may be set to start based on time intervals measured between a ventricular pacing pulse or sensed R-wave and the detected A1 event. The end of the A2 sensing window 422 may be set to start based on an A1-A2 time interval 432 or based on an A1-A3 time interval 434. It is recognized that numerous methods may be conceived for setting the A1, A2 and A3 sensing windows 420, 422 and 424, respectively, based on the consistency of the expected time intervals between any combinations of the ventricular electrical event (paced or sensed) and subsequent A1, A2 and A3 events. Furthermore, it is contemplated that these sensing windows 420, 422 and 424 may be set according to different control parameters, such as different fixed time intervals added to or subtracted from measured event time intervals depending on whether the ventricular electrical event is a paced or sensed event and/or depending on heart rate. The event time intervals that may be measured and used for setting the onset, offset and duration of the sensing windows 420, 422 and 424 may include any of the Vpace-A1, Vpace-A2, Vpace-A3, Rsense-A1, Rsense-A2, Rsense-A3, A1-A2, A1-A3, and/or A2-A3 time intervals determined during a paced and/or intrinsic rhythm.

The sensing threshold amplitudes 440, 442 and 444 may be set uniquely during each of the respective sensing windows 420, 422 and 424, respectively, or set to a fixed value for all sensing windows. The sensing threshold amplitudes 440, 442, and 444 may be fixed or decaying thresholds and may be automatically adjusted thresholds set to starting threshold values based on the peak motion sensor signal amplitude detected during each respective window 420, 422 and 424. The motion sensor signals 400 and 410 are shown as raw signals, but the motion sensor signal may be filtered, amplified and rectified by circuitry included in motion sensor 212 to provide control circuit 206 with a rectified signal that is used to detect the A1 through A4 events.

A post-ventricular, atrial refractory period 436 may be set based on the A1-A3 time interval 434 or based on the Vpace-A3 time interval (sum of Vpace-A1 interval 430 and A1-A3 time interval 434). In some examples, the atrial refractory period 436 ends upon the expiration of the A3 sensing window 424. In other examples, the atrial refractory period 436 ends after the expiration of the A3 sensing window 424. The A4 event 408 or 418 may be detected in response to the first positive-going crossing of an A4 sensing threshold amplitude 446 by the rectified motion sensor signal.

In some examples, the A4 detection is confirmed when the A1, A2 and A3 events have each been detected during the atrial refractory period 436. If any one of the A1, A2 or A3 events was not detected during the atrial refractory period 436, the A4 event detection based on a crossing of threshold 446 may not be confirmed and not used for starting an AV pacing interval. In other examples, at least one of the A1, A2 or A3 events may be required to be detected during a respective sensing window 420, 422, or 424 on a beat-by-beat basis for confirming an A4 detection after the atrial refractory period 436.

The A1, A2 and/or A3 events sensed during the respective A1 sensing window 420, A2 sensing window 422 and A3 sensing window 424 may be used for updating the atrial refractory period 436 as described in conjunction with FIG. 5 on a beat-by-beat or less frequent basis without requiring positive detection of each of A1, A2, and/or A3 for confirming an A4 detection on each beat. Setting the atrial refractory period based on detection and relative timing of the A1 through A3 events enables the atrial refractory period to be set based on the consistent timing of the ventricular motion sensor signal events so that A4 events may be detected with high reliability even when the timing of the A4 event relative to the A1-A3 events and the preceding ventricular electrical event is variable.

Figure 7:
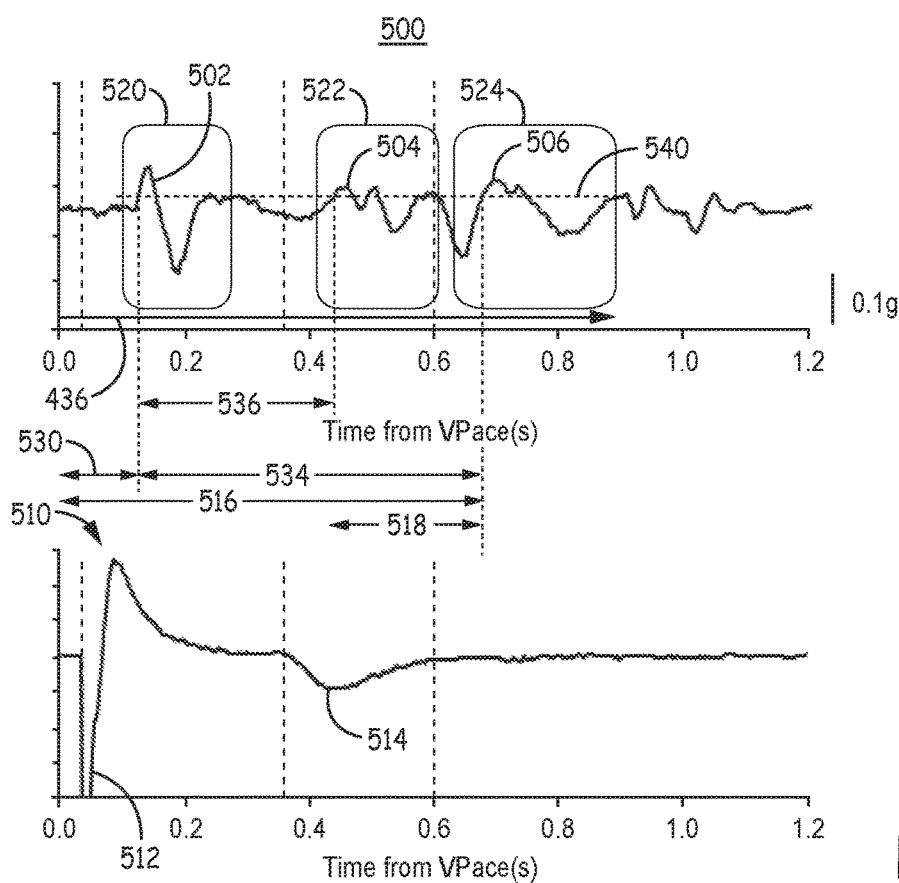
FIG. 7 is an averaged motion sensor signal.

FIG. 7 is an averaged motion sensor signal 500 that may be determined by control circuit 206 by averaging the motion sensor signal obtained over multiple cardiac cycles, e.g., signals 400 and 410 of FIG. 6. The averaged motion sensor signal 500 may represent the average of 3 to 20 or other predetermined number of cardiac cycles. The raw motion sensor signal or a filtered, amplified and/or rectified motion sensor signal may be buffered beginning from a ventricular electrical event, pacing pulse or sensed R-wave, at time 0.0 seconds until the next ventricular electrical event. The buffered motion sensor signal obtained over one cardiac cycle may be averaged with the buffered motion sensor signals obtained over a predetermined number of other cardiac cycles to produce averaged motion sensor signal 500.

A ventricular electrical signal 510 is shown aligned in time with averaged motion sensor signal 500. Ventricular electrical signal 510 may be passed from sensing circuit 204 to control module 206 and includes an R-wave 512, which may be an evoked or intrinsic R-wave, and a T-wave 514. R-wave 512 is followed by the ventricular contraction A1 event 502. The ventricular relaxation A2 event 504 occurs during T-wave 514. The passive ventricular filling A3 event 506 occurs after T-wave 514.

Since the A1, A2 and A3 events are ventricular mechanical events, they occur at consistent time intervals relative to each other and relative to ventricular electrical events (R-wave 512 and T-wave 514). As a result, the signal-to-noise ratio of the A1 signal 502, A2 signal 504 and A3 signal 506 is improved in the averaged motion sensor signal 500 compared to the single-cycle motion sensor signals 400 and 410 of FIG. 6. The averaged A1 event 502, A2 event 504 and A3 event 506 have an improved signal-to-noise ratio compared to the A1, A2 and A3 events observed in the motion sensor signal 400 or 410 of a single cardiac cycle as shown in FIG. 6, making A1, A2, and A3 event detection from the averaged motion signal 500 more reliable.

A single event detection threshold amplitude 540 may be defined such that the first positive-going crossing of the threshold 540 by the averaged, rectified motion sensor signal 500 within the A1 sensing window 520, A2 sensing window 522 and A3 sensing window 524 is detected as the respective A1 event 502, A2 event 504, and A3 event 506. Alternatively, unique detection threshold amplitudes may be defined for each sensing window 520, 522 and 524 for detecting the respective A1, A2 and A3 events. The sensing windows 520, 522 and 524 may be initially set according to expected A1, A2 and A3 event timing following the ventricular pacing pulse or R-wave 512 and may be adjusted according to the actual detection time of each respective A1 event 502, A2 event 504, and A3 event 506. The sensing windows 520, 522 and 524 may be set based on ventricular pacing rate or atrial event rate, e.g., based on A4-A4 event intervals. The sensing windows 520, 522 and 524 may also be set differently following a ventricular pacing pulse than following an intrinsic R-wave sensed event since the timing of the A1, A2 and A3 events and T-wave 514 may be altered during ventricular pacing compared to during an intrinsic ventricular rhythm.

The atrial systolic A4 event timing, which is independent of the ventricular electrical event timing, may be more variable from one cardiac cycle to the next with respect to the ventricular electrical and mechanical events, e.g., as shown by the relative timing of the A4 events 408 and 418 of signals 400 and 410 (FIG. 6). As a result, the A4 signal is largely attenuated in the averaged motion signal 500 in FIG. 7. The improved signal-to-noise ratio of the A1 through A3 events and attenuation of the A4 event in the averaged motion signal 500 enables control circuit 206 to reliably detect the signal averaged A1 event 502, A2 event 504 and A3 event 506 for determining one or more ventricular event time intervals for use in setting A1, A2 and A3 detection windows 420, 422, and 424, respectively, setting detection threshold amplitudes for detecting the A1, A2, A3 and/or A4 events, and/or setting atrial refractory period 436 used on a beat-by-beat basis for A4 event detection as shown in FIG. 6.

For example, a ventricular R-wave or pacing pulse to A1 time interval 530, an A1-A3 time interval 534, A1-A2 time interval 536, a ventricular R-wave or pacing pulse to A3 time interval 516, and/or a T-wave to A3 time interval 518 may be determined by control circuit 206 from the averaged motion signal 500 and the cardiac electrical signal 510. The atrial refractory period 436 is started upon delivering a ventricular pacing pulse or sensing an intrinsic R-wave. The atrial refractory period 436 may be set to expire after a predetermined time interval, e.g., 30 to 100 ms, after the A3 time interval 516. For instance, if time interval 516 is 700 ms, the atrial refractory period 436 may be set to expire 750 ms after the ventricular pacing pulse or sensed R-wave that started the atrial refractory period. Instead of using a time interval ending with the A3 event detection, a time interval ending with the A2 event detection may be determined and used in controlling the duration of the atrial refractory period 436. As described above, the A2 event, which occurs during T-wave 514, is an indicator of the end of ventricular mechanical systole and the onset of ventricular mechanical diastole. The A3 event occurs during ventricular mechanical diastole, during the passive ventricular filling phase. As such the timing of the A2 event 504 or the timing of the A3 event 506 relative to another ventricular electrical event (ventricular pacing pulse, R-wave 512, or T-wave 514) may be used for controlling the duration and expiration time of atrial refractory period 436. In other words, the timing of a ventricular mechanical diastolic event, A2 event 504 or A3 event 506, may be determined and used to set the atrial refractory period 436 that is applied on a beat-by-beat basis for detecting A4 events.

The T-wave 514 may be sensed by sensing circuit 206 on a beat-by-beat basis by control circuit 206 or by sensing circuit 204 from cardiac electrical signal 510. The T-wave 514 may be sensed at a maximum peak amplitude of a rectified cardiac electrical signal or a maximum absolute peak amplitude in a non-rectified cardiac signal received by control circuit 206 from sensing circuit 204. Alternatively, T-wave 514 may be sensed by sensing circuit 204 in response to the cardiac electrical signal crossing a T-wave sensing threshold amplitude after the ventricular pacing pulse or R-wave sensed event signal. In some cases, a T-wave sensing window may be applied after the R-wave sensed event signal or a delivered pacing pulse to facilitate T-wave sensing.

The T-wave 514 may be sensed during the atrial refractory period 436. Control circuit 206 may terminate the atrial refractory period 436 at a predetermined time interval after sensing T-wave 514. For instance if the T-wave to A3 time interval 518 is determined to be 150 ms from the averaged motion signal 500, control circuit 206 may terminate the atrial refractory period 436 at 180 ms after sensing the T-wave to promote reliable sensing of the A4 event.

Atrial event detector circuit 240 may be a processor-based circuit that determines the averaged motion sensor signal 500 over multiple cardiac cycles, detects A1, A2 and A3 events 502, 504, and 506 from the averaged motion sensor signal 500, and sets the atrial refractory period 436 based on the timing of at least one ventricular mechanical diastolic event, e.g., the A3 event 506, detected from the average motion sensor signal 500. In other examples, the A2 event is used as a ventricular diastolic mechanical event for marking the approximate timing of the onset of ventricular diastole. The A4 event, e.g., event 408 or 418 (FIG. 6) may be detected on a beat-by-beat basis from the non-averaged motion sensor signal after the atrial refractory period 436 expires.

Figure 8:
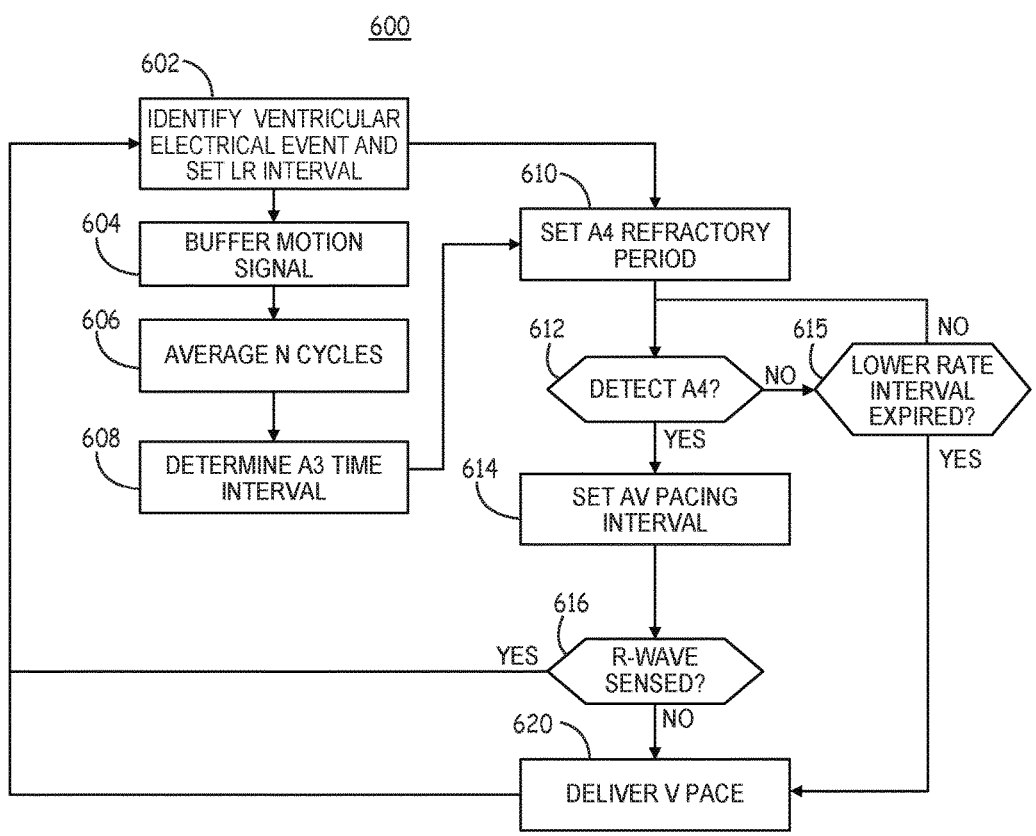
FIG. 8 is a flow chart of a method performed by an intracardiac ventricular pacemaker for detecting atrial events and controlling atrial-synchronized ventricular pacing according to another example.

FIG. 8 is a flow chart 600 of a method performed by pacemaker 14 for detecting atrial events and controlling atrial-synchronized ventricular pacing according to another example. At block 602, a ventricular electrical event is identified, which may be a sensed intrinsic R-wave or delivered ventricular pacing pulse. A lower rate pacing interval may be set at block 602 upon identifying the ventricular electrical event, as described in conjunction with FIG. 5, in order to maintain a minimum, base ventricular rate in the absence of A4 event detections.

At block 604, the motion sensor signal is buffered over the cardiac cycle, e.g., until the next ventricular electrical event is identified. At block 606, the buffered motion signal is averaged with buffered motion sensor signals acquired over a predetermined number of cardiac cycles to obtain an averaged motion signal with improved A1, A2 and A3 signal-to-noise ratio and attenuated A4 signal compared to the non-averaged motion sensor signal.

At block 608 the A1-A3 time interval or a ventricular electrical event to A3 time interval is determined from the averaged motion sensor signal by detecting the signal averaged A1, A2 and A3 events as described above in conjunction with FIG. 7. The A3 time interval is used to set the atrial refractory period at block 610 by atrial event detector circuit 240. As described above, the atrial refractory period may be set a predetermined percentage or fixed time interval longer than the A1-A3 time interval or a ventricular electrical event to A3 time interval or set to expire upon expiration of an A3 sensing window that is defined based on relative timing of the A1, A2, and A3 events. In other examples, an A2 time interval is determined at block 608 for use in setting the A4 refractory period. The A2 and A3 events are ventricular mechanical diastolic event markers that may be used for controlling the timing of the expiration of the A4 refractory period to occur near the start or during the ventricular passive filling phase, before the active ventricular filling phase associated with atrial systole.

The atrial refractory period is started at block 610 upon identifying a ventricular electrical event (pacing pulse or R-wave sensed event) at block 602. In some examples, signal averaging and determination of the A3 time interval (or A2 time interval) for setting the atrial refractory period may occur on a beat-by-beat basis using an averaged motion signal. In other examples, the A3 time interval is determined periodically or in response to a change in the atrial rate, e.g., determined from A4-A4 intervals, or a change between a sensed and paced ventricular rhythm. The most recently updated A3 time interval (or A2 time interval) determined from the averaged motion sensor signal may be used to set the atrial refractory period at block 610. The expiration of the atrial refractory period may be set on the fly during an already started atrial refractory period based on the A3 time interval determined during the current ventricular cycle. In other examples, the A3 time interval determined on a preceding ventricular cycle is used to set the atrial refractory period for the current ventricular cycle so that the atrial refractory period ends during or after an expected time of the A3 event, or in some cases prior to an expected A3 event but after an expected A2 event.

In other examples, the duration of the atrial refractory period may be controlled on a beat-by-beat basis by starting the atrial refractory period upon the identified ventricular event, sensing the T-wave during the atrial refractory period, and terminating the atrial refractory period a predetermined time interval after the sensed T-wave, where the predetermined time interval is based on the T-wave to A3 time interval 518 determined from the averaged motion signal 500 (FIG. 7).

If an A4 event is detected from the non-averaged motion sensor signal at block 612, after the atrial refractory period expires, an AV pacing interval is set at block 614. The A4 event may be detected based on an A4 detection threshold amplitude crossing by the raw motion sensor signal or by the rectified signal. The pace timing circuit 242 sets an AV pacing interval at block 614 in response to the detected A4 signal. If an intrinsic R-wave is not sensed before expiration of the AV pacing interval, as determined at block 616, the scheduled ventricular pacing pulse is delivered at block 620. In some cases, the A4 event may not be detected before a lower rate pacing interval expires at block 615. An atrial-asynchronous ventricular pacing pulse may be delivered at block 620 if the lower rate pacing interval expires before an A4 event is detected to maintain a programmed minimum ventricular base rate, causing the process to return to block 602 where the ventricular pacing pulse is identified as the next ventricular electrical event.

Figure 9:
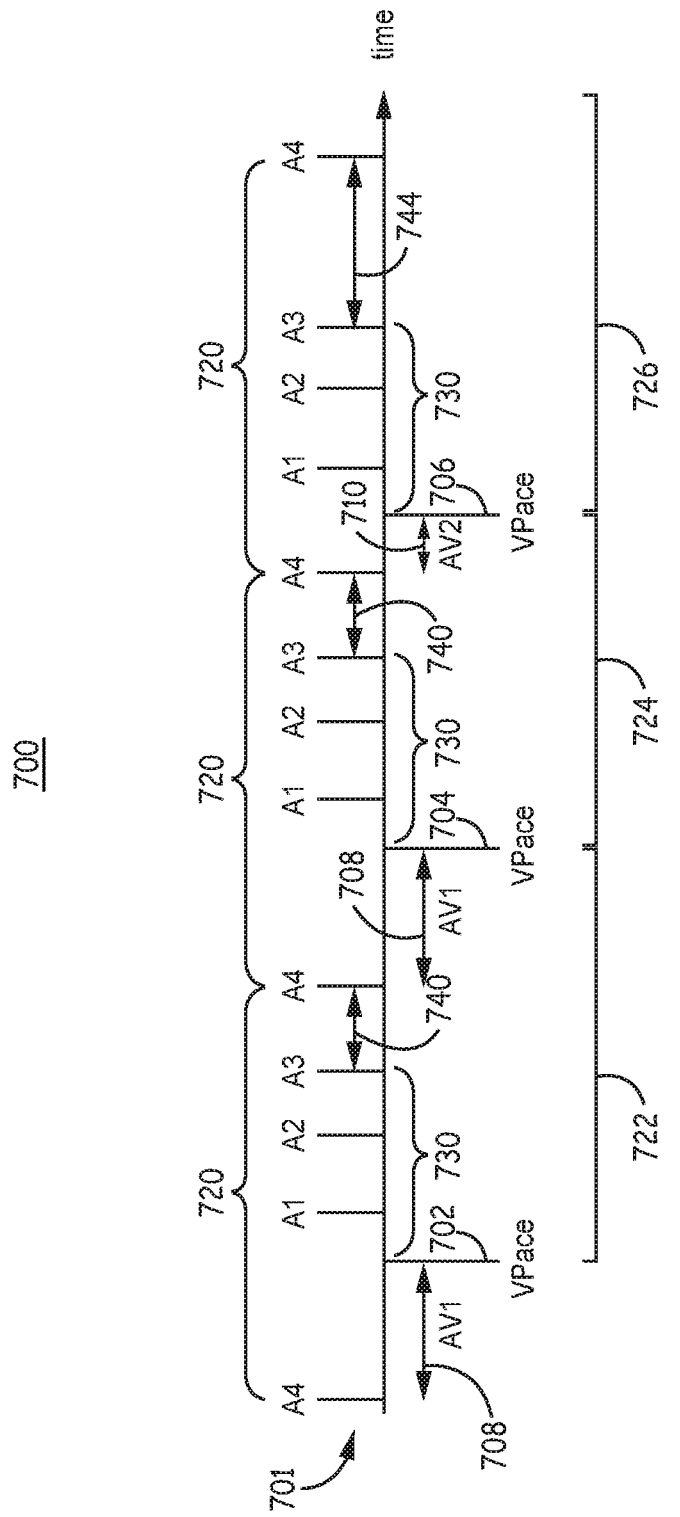
FIG. 9 is a timing diagram of sensed motion sensor signal events during ventricular pacing at two different AV pacing intervals.

FIG. 9 is a timing diagram 700 of sensed motion sensor signal events during ventricular pacing at two different AV pacing intervals. Timing markers 701 indicate the time that atrial event detector circuit 240 detects the A1, A2, A3 and A4 events from the motion sensor signal. The atrial rate is a stable intrinsic rate in this example such that the A4 events occur at regular A4-A4 intervals 720. The ventricular pacing pulses 702 and 704 are delivered at a first AV pacing interval (AV1) 708 following detected A4 events. The Vpace-A3 time interval 730 and the A3-A4 time interval 740 are consistent following pacing pulses 702 and 704.

The third ventricular pacing pulse 706 is delivered at a shortened AV pacing interval (AV2) 710. The ventricular cycle length 724 is shortened compared to the preceding ventricular cycle length 722 due to the earlier Vpace 706 at the shortened AV pacing interval 710. When the AV pacing interval is adjusted, the Vpace-A3 time interval 730 stays consistent between ventricular cycles 722, 724 and 726 since the A1, A2 and A3 events are ventricular mechanical events occurring as consequence of the electrical activation of the ventricle. The A4-A4 interval 720 remains unaffected by the change in AV pacing interval. As a result, the A3-A4 interval 744 is lengthened since the A3 event follows the earlier Vpace 706 at the shortened AV pacing interval 710.

This change in the A3-A4 time interval 744, or in the time between any of the ventricular events including the Vpace, A1, A2 and A3 events and the subsequent A4 event, caused by adjusting the AV pacing interval (during a stable atrial heart rate) may be determined by control circuit 206. If a change in the A3-A4 time interval 744 occurs as a result of changing the AV pacing interval, this change is evidence that the A4 event is a true A4 event. Adjustment of the AV pacing interval to check for a corresponding change in the A3-A4 time interval may be performed by control module 206 for verifying the detection of A4 events and avoiding false detections of A3 events as A4 events. During atrial-synchronized ventricular pacing, the AV pacing interval may be periodically adjusted to determine if the time interval between the Vpace or any of the A1, A2, or A3 events to the A4 event changes. If so, the event detected as the A4 event is confirmed. Determining that no change in the time interval from the Vpace to any of the A1, A2 and A3 events when the AV pacing interval is changed may be used to confirm the respective A1, A2 or A3 event or at least confirm that a detected motion sensor event is not an A4 event if the event is detected at a consistent time interval from the Vpace despite changes in the AV pacing interval.

Figure 10:
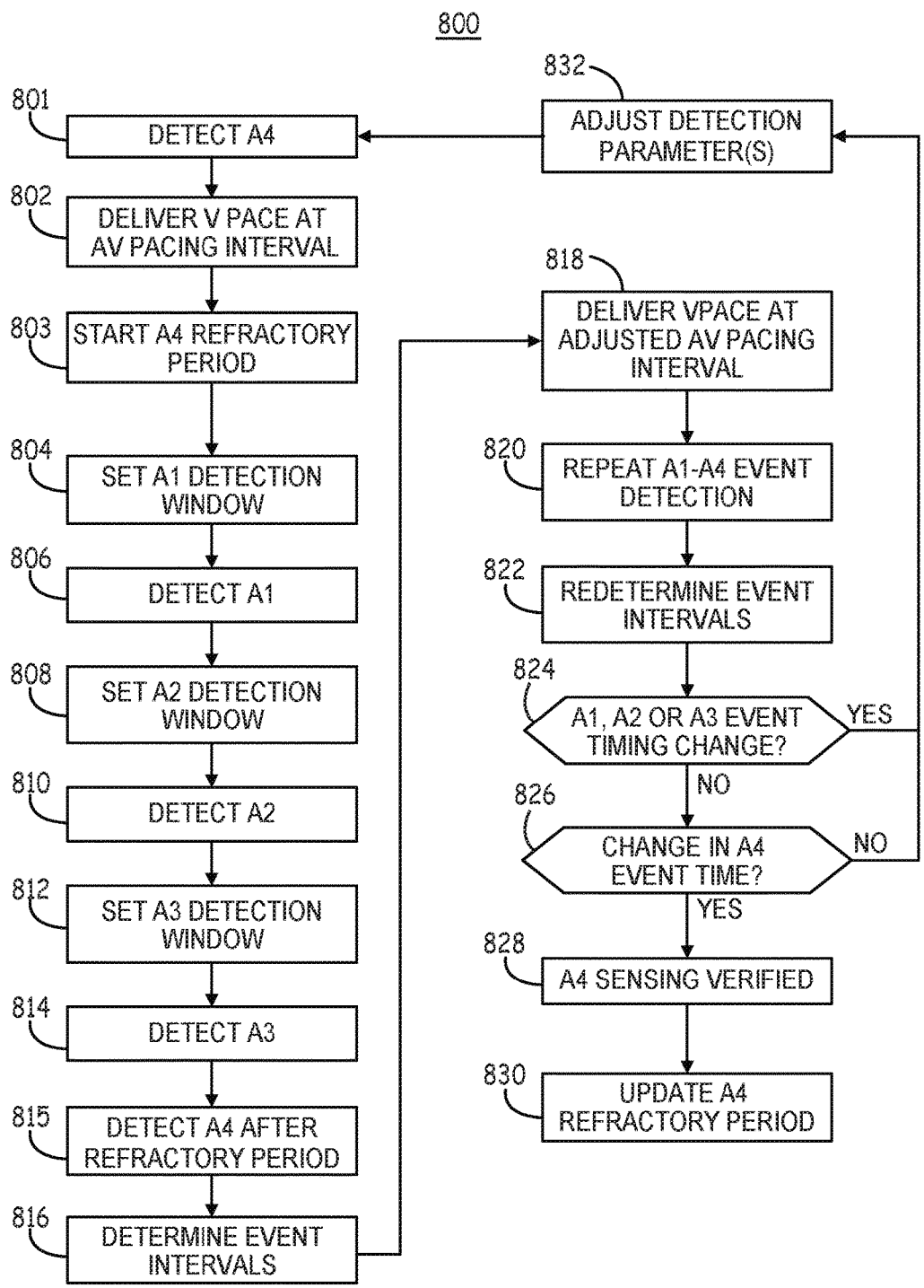
FIG. 10 is a flow chart of a method for updating an atrial refractory period by an intracardiac ventricular pacemaker.

FIG. 10 is a flow chart 800 of a method for updating the atrial refractory period by pacemaker 14. At block 801, an A4 event is detected using an initial atrial refractory period and A4 detection threshold amplitude. A ventricular pacing pulse is delivered at an AV pacing interval following the detected A4 event at block 802. Upon delivering the ventricular pacing pulse, the atrial refractory period is started at block 803, and an A1 detection window is set at block 804. The A1 detection window may be set according to an expected Vpace-A1 time interval, e.g., beginning 50 to 100 ms after the ventricular pacing pulse and ending 300 to 400 ms after the ventricular pacing pulse. The A1 event is detected during the A1 detection window at block 806 in response to a threshold amplitude crossing during the A1 detection window.

An A2 detection window is set at block 808. The A2 detection window may be set to start a predetermined interval after the ventricular pacing pulse, after the A1 detection, after the expiration of the A1 detection window, or at the expiration of the A1 detection window. The A2 detection window may begin 300 ms to 400 ms after the ventricular pacing pulse and end 500 to 600 ms after the ventricular pacing pulse. An A2 event is detected at block 810 in response to a threshold amplitude crossing of the motion sensor signal during the A2 detection window.

The A3 detection window is set at block 814 and may be based on the timing of the ventricular pacing pulse, a sensed T-wave, the A1 detection, the A2 detection or the expiration of the A2 detection window in various examples. The A3 detection window may begin 500 to 600 ms after the ventricular pacing pulse and end at 700 to 800 ms after the ventricular pacing pulse.

The examples of the starting and ending times of the A1, A2 and A3 detection windows given above are illustrative in nature and not intended to be limiting. The given examples may be applicable to a heart rate up to approximately 60 beats per minute. As heart rate increases, the Vpace-A3 interval is expected to decrease. As such, the A1, A2, and A3 detection windows may start and/or end earlier in time relative to the immediately preceding ventricular pacing pulse when the intrinsic atrial rate is faster, resulting in a faster ventricular pacing rate that is tracking the atrial A4 events.

At block 815, the next A4 event is detected after the atrial refractory period expires. The A4 event is detected in response to a threshold amplitude crossing of the motion sensor signal outside the atrial refractory period. The atrial refractory period may extend through at least a portion of the A3 detection window and may extend later than the A3 detection window. As described above, a single threshold amplitude may be used for detecting all A1 through A4 events or a unique threshold amplitude may be defined for detecting the A4 event outside the refractory period.

At block 816, detected event time intervals are determined. In one example, at least a Vpace-A3 time interval is determined for comparison to a Vpace-A3 time interval determined after adjusting the AV pacing interval as described below. In other examples, at least a T-wave to A3 time interval is determined. In still other examples, multiple time intervals may be determined between a ventricular electrical event and a ventricular mechanical event and/or between two ventricular mechanical events, e.g., between the ventricular pacing pulse or a sensed T-wave and one or more of the A1, A2 and A3 events and/or between one or more pairs of the A1, A2 and A3 events. Additionally, at least one time interval defined by the A4 event detection time is determined at block 816. For example, the A1-A4, A2-A4, A3-A4, Vpace-A4 and or T-wave-A4 time interval may be determined. These time intervals are stored in memory 210 for use in confirming the detected A4 event as described below.

The next ventricular pacing pulse is delivered at block 818 at an adjusted AV pacing interval. The AV pacing interval may be shortened by a predetermined interval compared to the AV pacing interval used at block 802. At block 820 the A1 through A4 events are detected and the event intervals determined at block 816 are re-determined at block 822 for the current ventricular cycle. The ventricular event intervals, e.g., any of the Vpace-A1, Vpace-A2, Vpace-A3, T-wave-A3, A1-A2, A1-A3, and/or A2-A3 event intervals, are re-determined to verify consistency in ventricular event interval(s) previously determined at block 816 and the ventricular event interval(s) determined at block 822. At block 824, comparisons are made between ventricular event intervals determined at block 816 and re-determined at block 822 after adjusting the AV pacing interval to verify that the ventricular event intervals are consistent despite the change in AV pacing interval. Verification of the ventricular event interval consistency provides confidence that none of the events detected as A1, A2 or A3 events are actually an atrial event. If a change in timing of any of the A1, A2 or A3 events is detected at block 824, the A1, A2 and/or A3 detection windows may be adjusted at block 832. In some examples, the detection threshold amplitude(s) used for detecting the A1, A2 and/or A3 events may also be adjusted.

At block 826, a time interval from any one of the ventricular events (Vpace, T-wave, A1, A2, or A3) to the A4 event is verified as being changed from an analogous time interval determined from the ventricular event to the atrial A4 event at block 816. The A4-A4 interval may also be determined at block 826 and compared to one or more preceding A4-A4 intervals or a running average A4-A4 interval to verify that the atrial rate is stable and unchanged. If the AV pacing interval is shortened, a time interval between a ventricular event, mechanical or electrical, and the A4 atrial event is expected to be lengthened by a corresponding amount if the atrial rate is unchanged. If the timing of the A4 event relative to a preceding ventricular event is not changed after adjusting the AV pacing interval, the detected A4 event may not be a true atrial event. A change in the A4 event timing may be detected if the A4 event time interval determined at block 822 is more than a threshold difference from the A4 event time interval determined at block 816.

For example, the A3 event may be falsely detected as the A4 event. The control circuit 206 may adjust the A1, A2, A3 detection windows and/or atrial refractory period at block 832 and repeat the process beginning at block 801. In some examples, the detection threshold amplitude used for detecting one or more of the A1 through A4 events may be adjusted at block 832 in addition to or instead of adjusting a detection window and/or atrial refractory period. Adjustments made at block 832 may be based on the event time interval determined at block 816. Alternatively, the methods described above in conjunction with FIG. 7 of obtaining an averaged motion signal 500 for detecting the A1, A2 and A3 events may be performed to reset the A1, A2 and A3 detection windows based on event time intervals determined from the averaged motion signal when the A4 event signal is attenuated.

If the ventricular event time intervals are verified as being unchanged at block 824 and a ventricular event to A4 time interval is verified as being increased at block 826, the A4 event detection is verified at block 828. The atrial refractory period may be updated at block 830 based on the Vpace-A3 time interval (or other A2 or A3 event time interval) and/or based on the ventricular event to A4 event time interval that was determined when the first, target AV pacing interval was used. The updated atrial refractory period is started upon the next ventricular pacing pulse or sensed R-wave. The A1, A2 and A3 event detection windows may also be updated at block 830 based on the timing of the detected A1, A2 and A3 events.

It is recognized that in some examples all three of the A1, A2 and A3 events may not be detected within a respective detection window during a given cardiac cycle. Detection of all three A1, A2 and A3 events sequentially during an atrial refractory period may provide greater confidence in an A4 event detection made outside the atrial refractory period on a given cardiac cycle. In some cases, however, detection of all three events is not necessary for confirming the A4 detection and updating detection windows and the atrial refractory period. For example, only an A3 detection window may be set for detecting the A3 event and determining a Vpace-A3 time interval. In other examples, all three detection windows may be set, and as long as at least one or more of the A1, A2 and A3 events is detected, a consistent ventricular event interval may be determined for use in confirming A4 detection and updating detection windows and the atrial refractory period.

The method of FIG. 10 may be performed on a periodic basis or in response to an atrial rate change (determined based on A4-A4 intervals) to enable adjustments to the A1, A2 and/or A3 detection windows and/or atrial refractory period to be made to promote reliable A4 event detection on an ongoing basis. Shifts in the timing of the A1 through A4 events with changes in heart rate or other factors may be accounted for by adjusting the detection windows and/or atrial refractory period before losing detection of any of the A1 through A4 events. In this way, reliable ongoing detection of the A4 atrial systolic events by ventricular pacemaker 14 enables appropriately timed, atrial-synchronized ventricular pacing pulses to be delivered.

Thus, various examples of an intracardiac pacemaker configured to deliver atrial-synchronized ventricular pacing have been described according to illustrative embodiments. In other examples, various methods described herein may include steps performed in a different order or combination than the illustrative examples shown and described herein. Furthermore, other circuitry may be conceived by one of ordinary skill in the art for implementing the techniques disclosed herein; the particular examples described herein are illustrative in nature and not intended to be limiting. It is appreciated that various modifications to the referenced examples may be made without departing from the scope of the disclosure and the following claims.

The invention claimed is:

1. An intracardiac ventricular pacemaker, comprising:
a pulse generator configured to generate and deliver pacing pulses to a ventricle of a patient's heart via electrodes coupled to the pacemaker;
a motion sensor configured to produce a motion signal comprising a ventricular diastolic event and an atrial systolic event; and
a control circuit coupled to the motion sensor and the pulse generator and configured to:
detect the ventricular diastolic event from the motion signal;
start an atrial refractory period having an expiration time set based on a time of the detection of the ventricular diastolic event;
detect a first atrial systolic event from the motion signal after expiration of the atrial refractory period; and
control the pulse generator to deliver a first pacing pulse to the ventricle at a first atrioventricular pacing time interval after the first atrial systolic event detection.

2. The pacemaker of claim 1, wherein the control circuit is configured to detect the ventricular diastolic event from the motion signal by detecting a ventricular passive filling event.

3. The pacemaker of claim 1, wherein the control circuit is further configured to start the atrial refractory period upon delivery of a preceding pacing pulse to the ventricle and end the atrial refractory period a predetermined time interval after detecting the ventricular diastolic event.

4. The pacemaker of claim 1, further comprising a sensing circuit configured to receive a cardiac electrical signal via electrodes coupled to the pacemaker;
wherein the control circuit is further configured to:
identify a ventricular electrical event, the ventricular electrical event being one of an R-wave of the cardiac electrical signal, a T-wave of the cardiac electrical signal, or a pacing pulse delivered by the pulse generator;
determine a time interval from the identified ventricular electrical event to the ventricular diastolic event; and
set the atrial refractory period based on the determined time interval.

5. The pacemaker of claim 1, further comprising a sensing circuit configured to receive a cardiac electrical signal comprising R-waves via electrodes coupled to the pacemaker;
wherein the control circuit is further configured to:
identify a ventricular electrical event, the ventricular electrical event being one of an R-wave of the cardiac electrical signal and a pacing pulse delivered by the pulse generator;
set a plurality of ventricular mechanical event detection windows in response to identifying the ventricular electrical event, the plurality of ventricular mechanical event detection windows comprising a first detection window set based on an estimated time of a ventricular contraction event of the motion signal, a second detection window set based on an estimated time of a ventricular relaxation event of the motion signal and a third detection window set based on an estimated time of a ventricular passive filling event of the motion signal; and
confirm detection of the atrial systole detection after expiration of the atrial refractory period in response to detecting at least one of the ventricular contraction event, the ventricular relaxation event, and the ventricular passive filling event during the respective first, second and third detection windows.

6. The pacemaker of claim 1, wherein the control circuit is further configured to:

receive the motion signal over a plurality of ventricular cycles;

average the motion signal over the plurality of ventricular cycles;

detect the ventricular diastolic event from the averaged motion signal;

determine a time interval ending at the detected ventricular diastolic event; and set the expiration time of the atrial refractory period based on the determined time interval.

7. The pacemaker of claim 1, wherein the control circuit is further configured to:

detect a first ventricular mechanical event from the motion sensor signal during a first ventricular cycle following the first ventricular pacing pulse;

determine a first ventricular event time interval from the first ventricular pacing pulse to the first ventricular mechanical event;

detect a second atrial systolic event from the motion signal;

control the pulse generator to deliver a second pacing pulse to the ventricle at a second atrioventricular pacing time interval after the second atrial systolic event detection, the second atrioventricular pacing time interval different than the first atrioventricular pacing time interval;

detect a second ventricular mechanical event from the motion sensor signal during a second ventricular cycle following the second ventricular pacing pulse;

determine a second ventricular event time interval from the second pacing pulse to the second ventricular mechanical event;

detect a third atrial systolic event from the motion signal; and confirm detection of the third atrial systolic event in response to the second ventricular event time interval being unchanged from the first ventricular event time interval.

8. The pacemaker of claim 7, wherein the control circuit is further configured to confirm the detection of the third atrial systolic event by:

determining a first ventricular-to-atrial event time interval from the first atrial systolic event to a preceding one of the first ventricular pacing pulse and a first ventricular mechanical event detected from the motion sensor signal during the first ventricular cycle;

determining a second ventricular-to-atrial event time interval from the second atrial systolic event to a preceding one of the second ventricular pacing pulse and a second ventricular mechanical event detected from the motion sensor signal during the second ventricular cycle; and detecting a change in the second ventricular-to-atrial event time interval from the first ventricular-to-atrial event time interval.

9. The pacemaker of claim 1, wherein the control circuit is further configured to:

receive the motion signal over a plurality of ventricular cycles;

average the motion signal over the plurality of ventricular cycles;

set a sensing window;

detect the ventricular diastolic event from the averaged motion signal during the sensing window;

determine a time interval ending at the detected ventricular diastolic event; and set the atrial refractory period to end later than the determined time interval, the ventricular diastolic event being one of a ventricular relaxation event and a ventricular passive filling event.

10. The pacemaker of claim 1, further comprising:

a housing enclosing the pulse generator, the motion sensor and the control circuit; and a cathode electrode and anode electrode carried by the housing and coupled to the pulse generator for delivering the first pacing pulse to the patient's ventricle.

11. A method performed by an intracardiac pacemaker, comprising:

detecting by a control circuit of the pacemaker a ventricular diastolic event from a motion signal received by the control circuit from a motion sensor;

starting an atrial refractory period having an expiration time set based on a time of the detection of the ventricular diastolic event;

detecting a first atrial systolic event from the motion signal after expiration of the atrial refractory period; and controlling a pulse generator of the pacemaker to deliver a first pacing pulse to a ventricle of a patient's heart at a first atrioventricular pacing time interval after the first atrial systolic event detection.

12. The method of claim 11, wherein detecting the ventricular diastolic event from the motion signal comprises detecting a ventricular passive filling event.

13. The method of claim 11, further comprising starting the atrial refractory period upon delivery of a preceding pacing pulse to the ventricle and ending the atrial refractory period a predetermined time interval after detecting the ventricular diastolic event.

14. The method of claim 11, further comprising:

receiving a cardiac electrical signal by a sensing circuit of the pacemaker;

identifying a ventricular electrical event, the ventricular electrical event being one of an R-wave of the cardiac electrical signal, a T-wave of the cardiac electrical signal, or a pacing pulse delivered by the pulse generator ;

determining a time interval from the identified ventricular electrical event to the ventricular diastolic event; and set the atrial refractory period based on the determined time interval.

15. The method of claim 11, further comprising:

receiving a cardiac electrical signal comprising R-waves by a sensing circuit of the pacemaker;

identifying a ventricular electrical event, the ventricular electrical event being one of an R-wave of the cardiac electrical signal and a pacing pulse delivered by the pulse generator;

setting a plurality of ventricular mechanical event detection windows in response to identifying the ventricular electrical event, the plurality of ventricular mechanical event detection windows comprising a first detection window set based on an estimated time of a ventricular contraction event of the motion signal, a second detection window set based on an estimated time of a ventricular relaxation event of the motion signal and a third detection window set based on an estimated time of a ventricular passive filling event of the motion signal; and confirming detection of the atrial systolic event after expiration of the atrial refractory period in response to detecting at least one of the ventricular contraction event, the ventricular relaxation event, and the ventricular passive filling event during the respective first, second and third detection windows.

16. The method of claim 11, further comprising:
receiving the motion signal over a plurality of ventricular cycles;
averaging the motion signal over the plurality of ventricular cycles;
detecting the ventricular diastolic event from the averaged motion signal; determining a time interval ending at the detected ventricular diastolic event; and
setting the expiration time of the atrial refractory period based on the determined time interval.

17. The method of claim 11, further comprising:
detecting a first ventricular mechanical event from the motion sensor signal during a first ventricular cycle following the first ventricular pacing pulse;
determining a first ventricular event time interval from the first ventricular pacing pulse to the first ventricular mechanical event;
detecting a second atrial systolic event from the motion signal;
controlling the pulse generator to deliver a second pacing pulse to the ventricle at a second atrioventricular pacing time interval after the second atrial systolic event detection, the second atrioventricular pacing time interval different than the first atrioventricular pacing time interval;
determining a second ventricular event time interval from the second pacing pulse to one of the ventricular contraction event, the ventricular relaxation event, and the ventricular passive filling event during a second ventricular cycle following the second ventricular pacing pulse;
detecting a third atrial systolic event from the motion signal; and
confirming detection of the third atrial systolic event in response to the second ventricular event time interval being unchanged from the first ventricular event time interval.

18. The method of claim 17, wherein confirming the detection of the third atrial systolic event further comprises:
determining a first ventricular-to-atrial event time interval from the first atrial systolic event to a preceding one of the first ventricular pacing pulse and a first ventricular mechanical event detected from the motion sensor signal during the first ventricular cycle;
determining a second ventricular-to-atrial event time interval from the second atrial systolic event to a preceding one of the second ventricular pacing pulse and a second ventricular mechanical event detected from the motion sensor signal during the second ventricular cycle; and
detecting a change in the second ventricular-to-atrial event time interval from the first ventricular-to-atrial event time interval.

19. The method of claim 11, further comprising:
receiving the motion signal over a plurality of ventricular cycles;
averaging the motion signal over the plurality of ventricular cycles;
setting a sensing window;
detecting the ventricular diastolic event from the averaged motion signal during the sensing window;
determining a time interval ending at the detected ventricular diastolic event; and
setting the atrial refractory period to end later than the determined time interval, the ventricular diastolic event being one of a ventricular relaxation event and a ventricular passive filling event.

20. The method of claim 11, further comprising:
delivering the first pacing pulse to the patient's ventricle via a cathode electrode and anode electrode carried by a housing of the pacemaker that encloses the pulse generator, the motion sensor and the control circuit.

21. A non-transitory computer-readable medium storing a set of instructions which when executed by a control circuit of an intracardiac ventricular pacemaker having a motion sensor, cause the pacemaker to:
detect a ventricular diastolic event from a motion signal produced by the motion sensor;
start an atrial refractory period having an expiration time set based on a time of the detection of the ventricular diastolic event;
detect an atrial systolic event from the motion signal after expiration of the atrial refractory period; and
control a pulse generator of the pacemaker to deliver a pacing pulse to a ventricle of a patient's heart at an atrioventricular pacing time interval after the atrial systolic event detection.

22. The pacemaker of claim 1, wherein to detect the ventricular diastolic event from the motion signal, the control circuit is configured to detect the ventricular diastolic event based on determining that the motion signal is greater than at least one threshold for the ventricular diastolic event.

* * * * *